United States Patent
Pandolfi et al.

(12)

(10) Patent No.: US 6,262,116 B1
(45) Date of Patent: Jul. 17, 2001

(54) TRANSCRIPTION THERAPY FOR CANCERS

(75) Inventors: Pier Paolo Pandolfi, New York, NY (US); Raymond P. Warrell, Jr., Westfield, NJ (US); Arthur Zelent, London (GB)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/154,672

(22) Filed: Sep. 18, 1998

Related U.S. Application Data
(60) Provisional application No. 60/072,279, filed on Jan. 23, 1998.

(51) Int. Cl.[7] ............................. A61K 31/19; A01N 37/00
(52) U.S. Cl. .............................................. 514/557
(58) Field of Search ............................................. 514/557

(56) References Cited

PUBLICATIONS

He, L. Z. et al., "Distinct interaction sof PML–RARalpha and PLZF–RARalpha with co–repressors determin differential responses to RA in APL.", Abstract to Nature Genetics, 18(2), pp. 126–135, Feb. 1998.*

Chen, Alex et al., "Retinoic Acid is required for and potentidates differentidationof acute promyelocytic leukemia cells by nonretinoid agents", Abstract to Blood, 84(7), pp. 2122–2129, 1994, Feb. 1998.*

\* cited by examiner

*Primary Examiner*—Dwayne C. Jones
(74) *Attorney, Agent, or Firm*—John P. White; Cooper & Dunham LLP

(57) ABSTRACT

The present invention provides method of treating a neoplastic condition in an individual, comprising the step of administering to said individual a pharmacologically effective dose of a retinoic acid and/or an inhibitor of histone deacetylase. Also provided is a pharmaceutical composition, comprising a retinoic acid, an inhibitor of histone deacetylase and a pharmaceutically acceptable carrier. Further provided is a method of inducing terminal differentiation of tumor cells in a tumor in an individual in need of such treatment, comprising the step of administering to said individual a pharmacologically effective dose of a retinoic acid and/or an inhibitor of histone deacetylase.

3 Claims, 28 Drawing Sheets

TRANSCRIPTION THERAPY FOR CANCERS

CROSS-REFERENCE TO RELATED APPLICATION

This application claims the benefit of provisional application Ser. No. 60/072,279, filed Jan. 23, 1998, now abandoned.

FEDERAL FUNDING LEGEND

This invention was created in part using funds from the National Institutes of Health under grant CA74031-01. The federal government, therefore, has certain rights in this invention.

BACKGROUND OF THE INVENTION

1. Field of the Invention

The present invention relates generally to the fields of molecular biology of cancers. More specifically, the present invention relates to a method of transcription therapy for cancers.

2. Description of the Related Art

Acute promyelocytic leukaemia (APL) is characterized by the clonal expansion of malignant myeloid cells blocked at the promyelocytic stage of hemopoietic development[1,2]. APL is associated with reciprocal chromosomal translocations always involving the retinoic acid receptor-α (RAR-α) gene on chromosome 17, that variably translocates to the promyelocytic leukaemia (PML) gene on chromosome 15, or the PLZF [Promyelocytic Leukaemia Zinc Finger; ZNF145 in the Human Genome Organization (HUGO) nomenclature] gene on chromosome 11 (for brevity referred to hereafter as X genes[3-10]).

PML is a member of the RING finger family of proteins[11]. The PLZF gene encodes a transcription factor with transcriptional repressive activity, and is a member of the POK (POZ and Krüppel) family of proteins which share an N-terminal POZ motif and a C-terminal DNA binding domain made by Krüppel-like C2-H2 zinc-fingers[9,12]. Although structurally unrelated, promyelocytic leukaemia and promyelocytic leukaemia zinc finger heterodimerize and co-localize in the nucleus onto structures known as nuclear bodies[13].

Retinoic acid receptors are members of the superfamily of nuclear hormone receptors which act as retinoic acid-inducible transcriptional activators, in their heterodimeric form with retinoid-X-receptors (RXRs), a second class of nuclear retinoid receptors[14]. In the absence of retinoic acid, retinoic acid receptor/Retinoid-X-Receptors heterodimers can repress transcription through histone deacetylation by recruiting nuclear receptor co-repressors (N-CoR or SMRT), Sin3A or Sin3B, which in turn form complexes with histone deacetylases (histone deacetylases 1 or 2), thereby resulting in nucleosome assembly and transcriptional repression[15]. Retinoic acid causes the dissociation of the co-repressors complex, and the recruitment of transcriptional co-activators to the retinoic acid receptor/retinoid-X-receptor complex, thus resulting in the activation of gene expression which induces terminal differentiation and growth arrest of cells of various histological origin including normal myeloid hemopoietic cells[16,17].

The X-retinoic acid receptor-α and retinoic acid receptor-α-X fusion genes generated by the reciprocal translocation in APL encode for structurally different X-retinoic acid receptor-α and retinoic acid receptor-α-X products, co-expressed in the leukaemic blast, which differ in their X portions, but are identical in their retinoic acid receptor-α portion, and that can therefore be considered as retinoic acid receptor0α mutants[3,4].

APL is uniquely sensitive to the differentiating action of retinoic acid (RA), becoming the paradigm for cancer differentiation therapy[1,2,18]. Unlike other APLs, leukaemias characterized by translocations between PLZF and retinoic acid receptor-α genes do not respond or respond poorly to retinoic acid, thus defining a new APL syndrome[19]. In these patients, resistance to retinoic acid could be conferred by the PLZF-retinoic acid receptor-α protein itself, or by the retinoic acid receptor-α-PLZF fusion protein which could function as an aberrant transcription factor since it retains part of the PLZF DNA binding domain and still binds to PLZF DNA binding sites[12].

PML-retinoic acid receptor-α and PLZF-retinoic acid receptor-α are both able to bind to retinoic acid response elements (retinoic acid receptorE) as homodimers, and can form multimeric complexes with Retinoid-X-Receptors[20-23]. Therefore, X-retinoic acid receptor-α is thought to interfere with the normal retinoic acid receptor-α/Retinoid-X-Receptor-retinoic acid pathway in a dominant negative manner through its ability to complex with Retinoid-X-Receptors, and/or through its altered DNA binding and transcriptional activities[5-7,22-25]. PML-retinoic acid receptor-α and PLZF-retinoic acid receptor-α can also heterodimerize with promyelocytic leukaemia and PLZF, thus acting in principle as double dominant negative oncogenic products, interfering with both X and retinoic acid receptor-α/retinoid-X-receptor-retinoic acid-α pathways[13,26-28].

However, promyelocytic leukaemia-retinoic acid receptor-α and PLZF-retinoic acid receptor-α proteins retain intact retinoic acid receptor-α DNA and ligand binding domains, and have an affinity for the ligand comparable to that of the wild-type retinoic acid receptor-α[29,30]. Therefore, the molecular mechanisms by which both X-retinoic acid receptor-α molecules would be leukemogenic at physiological doses of retinoic acid, and would behave differently at pharmacological doses of retinoic acid, remains unexplained. As a more fundamental corollary, it is unclear if APL is caused by the aberrant retinoic acid-dependent transactivation of gene expression by X-retinoic acid receptor-α proteins since in this case APL should always be exacerbated by retinoic acid. On the contrary and paradoxically, retinoic acid is extremely effective in APL cases harboring promyelocytic leukaemia-retinoic acid receptor-α. Thus, the elucidation of the molecular basis of the differential responses to retinoic acid in APL, is crucial for the understanding of APL pathogenesis itself, and goes beyond simply clarifying the mechanisms which underlay retinoic acid resistance in APL.

The BCL-6 proto-oncogene is involved in diffuse large cell lymphoma and rearrangements of the BCL-6 gene are found in 30–40% of diffuse large cell lymphomas. The BCL-6 gene functions as a strong transcriptional repressor of promoters linked to its DNA target sequence. The BCL-6 gene functions as a transcriptional switch that controls germinal centre formation and altered expression of the BCL-6 gene appears to be important in lymphoma.

Until recently, the mechanism whereby oncogenes suppressed mRNA transcription of target genes was poorly understood. The enzymatic addition of acetyl groups to histones, nuclear proteins closely associated with DNA, is known to have a permissive effect for mRNA transcription[15], probably by relaxing specific segments of tightly coiled DNA which facilitates binding of transcription factors[61]. Recently, several laboratories showed that certain oncogenes suppressed transcription of their target genes by recruiting histone deacetylases[62-64] that cleaved acetyl groups from histones and blocked the DNA conformational change. Experimentally, this transcriptional blockade could be overcome by agents that inhibited the enzyme.

Earlier this year, several laboratories reported that the oncoprotein encoded by the chromosomal translocation in acute promyelocytic leukemia suppresses transcription by recruitment of a histone deacetylase[65-67]. Furthermore, resistance to the cytodifferentiating actions of all-trans retinoic acid in cell lines derived from patients with acute promyelocytic leukemia could be overcome by co-treatment with an inhibitor of histone deacetylase[65-67]. Since butyric acid was known to inhibit histone deacetylase[68], sodium phenylbutyrate, a drug previously tested for treatment of thalassemia[69] and certain hyperammonemic states[70], was tested against promyelocytic leukemia.

The prior art is deficient in the lack of effective means of treating APL that is resistant to retinoic acid therapy. The present invention fulfills this longstanding need and desire in the art.

SUMMARY OF THE INVENTION

In one embodiment of the present invention, there is provided a method of treating a tumor in an individual, comprising the step of administering to said individual a pharmacologically effective dose of an inhibitor of histone deacetylase.

In one embodiment of the present invention, there is provided a method of treating a tumor in an individual, comprising the step of administering to said individual a pharmacologically effective dose of a retinoid and an inhibitor of histone deacetylase.

In one embodiment of the present invention, there is provided a method of treating APL in an individual, comprising the step of administering to said individual a pharmacologically effective dose of an inhibitor of histone deacetylase.

In one embodiment of the present invention, there is provided a method of treating APL in an individual, comprising the step of administering to said individual a pharmacologically effective dose of a retinoid and an inhibitor of histone deacetylase.

In another embodiment of the present invention, there is provided a pharmaceutical composition, comprising a retinoid, an inhibitor of histone deacetylase and a pharmaceutically acceptable carrier.

In yet another embodiment of the present invention, there is provided a method of antagonizing X-retinoic acid receptor-α transcriptional repression and concomitantly inducing the retinoic acid dependent transactivation of retinoic acid target genes by retinoic acid receptor-α/retinoid-X-receptor-α and/or by X-retinoic acid receptor-α proteins themselves.

In yet another embodiment of the present invention, there is provided a method of inducing differentiation of tumor cells in a tumor in an individual in need of such treatment, comprising the step of administering to said individual a pharmacologically effective dose of an inhibitor of histone deacetylase.

In yet another embodiment of the present invention, there is provided a method of inducing differentiation of tumor cells in a tumor in an individual in need of such treatment, comprising the step of administering to said individual a pharmacologically effective dose of a retinoid and an inhibitor of histone deacetylase.

In yet another embodiment of the present invention, there is provided a method of treating APL in an individual, comprising the step of administering to said individual a pharmacologically effective dose of a retinoid and sodium phenylbutyrate.

Acute promyelocytic leukaemia associated with chromosomal translocations involving the retinoic acid receptor-α gene and the promyelocytic leukaemia gene is sensitive to retinoic acid treatment, while APL patients harboring translocations between the retinoic acid receptor gene and the PLZF gene do not respond to retinoic acid. PML-retinoic acid receptor and PLZF-retinoic acid receptor transgenic mice were generated and these fusion proteins play a critical role in leukaemogenesis and in determining responses to retinoic acid in APL. PLZF-retinoic acid receptor mice developed retinoic acid-resistant leukaemia, while promyelocytic leukaemia-retinoic acid receptor-α mice were responsive to retinoic acid treatment. Both promyelocytic leukaemia-retinoic acid receptor-α and PLZF-retinoic acid receptor-α fusion proteins can act as transcriptional repressors and were able to interact with nuclear receptor transcriptional co-repressors such as SMRT. However, PLZF-retinoic acid receptor-α, unlike promyelocytic leukaemia-retinoic acid receptor-α, can form, via its PLZF moiety, co-repressor complexes which are insensitive to retinoic acid. Histone deacetylase inhibitors such as Trichostatin A, in combination with retinoic acid, can overcome the transcriptional repressive activity of promyelocytic leukaemia-retinoic acid receptor and PLZF-retinoic acid receptor as well as the irresponsiveness of PLZF-retinoic acid receptor leukaemic cells to retinoic acid. Clinical use of a histone deacetylase inhibitor induces chromatin hyperacetylation in target cells and can restore sensitivity to all-trans retinoic acid in acute promyelocytic leukemia. Similar treatment may prove useful in other neoplastic diseases that are associated with oncogenic repression of gene transcription due to recruitment of histone deacetylases. Thus, these findings unravel a crucial role for transcriptional silencing in APL and cancer pathogenesis and resistance to retinoic acid in APL and in cancers in general.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the generation of hCG-X-retinoic acid receptor-α transgenic mice.

FIG. 4 shows an in vivo differential response to retinoic acid in leukaemia from X-retinoic acid receptor-α transgenic mice.

FIG. 5C shows the levels of expression of promyelocytic leukaemia-retinoic acid receptor-α and PLZF-retinoic acid receptor-α obtained upon transient transfection of 293T cells. 10 ml of 293T cell nuclear extracts transfected with either the promyelocytic leukaemia-retinoic acid receptor-α expression vector (1), or the PLZF-retinoic acid receptor-α expression vector (2), from the experiment shown in FIG. 5A, were resolved on a 10% SDS-PAGE gel, transferred and immunoblotted with an anti-retinoic acid receptor-α antibody to the retinoic acid receptor F region. In the experiments shown, with or without retinoic acid, no significant difference was observed between the levels of expression of the two retinoic acid receptor-α fusion proteins.

FIG. 6 shows distinct interactions of X-retinoic acid receptor-α proteins with nuclear co-repressors.

FIG. 7 shows high dose retinoic acid induces clinical remission in PLZF-retinoic acid receptor-α transgenic mice. Mice were treated daily with 7.5 mg retinoic acid per gram of mouse body weight, a dose five times greater than the dose utilized for the retinoic acid trials in human APL.

DETAILED DESCRIPTION OF THE INVENTION

Figure 1A:
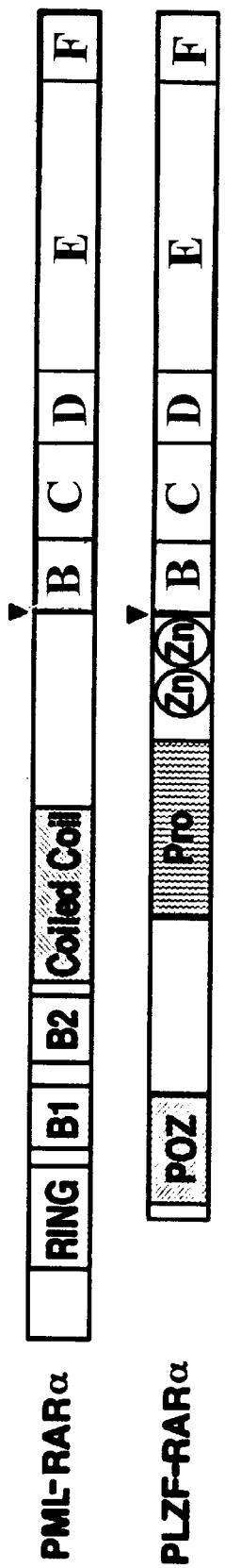
FIG. 1A shows the modular organization of the promyelocytic leukaemia-retinoic acid receptor-α and PLZF-retinoic acid receptor-α fusion proteins. Retinoic acid receptor-α is subdivided into its conserved functional domains: C and E identify the DNA and Ligand binding domains respectively. The breakpoints where promyelocytic leukaemia or PLZF fuse to retinoic acid receptor-α are indicated by the black arrowheads. The various functional regions from the promyelocytic leukaemia and PLZF proteins retained in the X-retinoic acid receptor-α fusion proteins are also indicated. RING designates the RING-finger domain which together with two additional Zinc fingers (B-Boxes 1 and 2: B1 and B2), identify a promyelocytic leukaemia protein-protein interaction interface. The coiled coil region retains the promyelocytic leukaemia homodimerization interface. The POZ domain, a proline rich regions (Pro) and the first two Zinc-fingers (Zn) from the PLZF protein are also shown.

As used herein, the term "promyelocytic leukaemia or PML" shall refer to a gene involved in the chromosomal translocation between chromosomes 15 and 17 which characterizes APL.

As used herein, the term "promyelocytic leukaemia zinc finger or PLZF" shall refer to a gene involved in the chromosomal translocation between chromosomes 11 and 17 which characterized APL.

As used herein, the term "cancer differentiation therapy" shall refer to a treatment that, unlike other cancer therapies, does not intend to kill tumoral cells but to induce their terminal differentiation thus resulting in the exhaustion of the malignant cellular compartment.

As used herein, the term "retinoic acid resistance" shall refer to resistance to the differentiating activity of retinoic acid.

As used herein, the term "transcriptional repressive activity" or "transcriptional silencing" shall refer to the ability of certain proteins to repress the transcription of specific genes.

As used herein, the term "differential repressive activity" shall refer to fusion proteins associated with APL pathogenesis that have a different ("differential") ability to repress the transcription of certain genes.

As used herein, the term "nuclear receptor co-repressors" shall refer to specific proteins that can enhance the ability of other proteins to repress transcription.

As used herein, the term "promyelocytic leukaemia-retinoic acid receptor-α" shall refer to a fusion protein (PML-RARα) identified in the leukemic cells of patients affected by acute promyelocytic leukemia (APL) with a translocation between chromosomes 15 and 17.

As used herein, the term "PLZF-retinoic acid receptor-α" shall refer to a fusion protein (PLZF-RARα) identified in the leukemic cells of patients affected by (APL) with a translocation between chromosomes 11 and 17.

As used herein, the term "X-retinoic acid receptor-α" shall refer to fusion proteins (X-RARα) identified in the leukemic cells of patients affected by (APL) with a translocation between chromosomes 11, 15, 5 and 17.

As used herein, the term "BTB/POZ domain" shall refer to a protein domain that confers to the protein in question the ability to repress transcription of specific genes.

As used herein, the term "hCG-PLZF-retinoic acid receptor-α transgenic mice" shall refer to a construct that enables expression in vivo in the mouse of the PLZF-RARα fusion protein in a specific subset of cells (promyelocytes).

As used herein, the term "retinoid" shall refer to a derivative of vitamin A that binds to retinoid receptors.

As used herein, the term "triggering agent" shall refer to a chemical compound or biological agent that directly or indirectly stimulates activation or mRNA transcription. A representative use of a "triggering agent" is the use of all-trans retinoic acid in APL. Other "triggering agents" include vitamin D and its analogs.

The present invention defines the mechanisms of transcriptional repression by X-retinoic acid receptor-α fusion proteins in a unified model explaining both the molecular pathogenesis of APL and the differential response to retinoic acid in APL. In transgenic mice in which promyelocytic leukaemia-retinoic acid receptor-α and PLZF-retinoic acid receptor-α are specifically expressed in the promyelocytic cellular compartment, both X-retinoic acid receptor-α proteins play a crucial leukemogenic role, but these X-retinoic acid receptor-α protein retain intrinsic biological differences conferred by their different X moieties resulting in a differential response to retinoic acid. In the absence of retinoic acid, both promyelocytic leukaemia-retinoic acid receptor-α and PLZF-retinoic acid receptor-α can form a complex with transcriptional co-repressors, and act as potent transcriptional repressors.

Pharmacological doses of retinoic acid induce the dissociation of promyelocytic leukaemia-retinoic acid receptor-α co-repressor complexes partially overcoming this transcriptional block, while PLZF-retinoic acid receptor-α can form complexes which are, at these doses, insensitive to retinoic acid. The differential repressive activity by X-retinoic acid receptor-α proteins correlates inversely with the ability of retinoic acid to induce in vivo clinical remission in leukaemias from X-retinoic acid receptor-α transgenic mice. Furthermore, histone deacetylases inhibitors such as Trichostatin A[31], in combination with retinoic acid, overcame transcriptional repression and irresponsiveness to retinoic acid in APL. It is reported herein that phenylbutyrate acts synergistically with all-trans retinoic acid in vitro to increase cytodifferentiation of acute promyelocytic leukemia cell lines. Furthermore, clinical treatment with phenylbutyrate induces histone hyperacetylation in nucleated blood and bone marrow cells at plasma concentrations that are readily achieved in vivo. Finally, phenylbutyrate, when used in combination with all-trans retinoic acid, induced a complete clinical and molecular remission in a patient with acute promyelocytic leukemia who had been highly resistant to all other forms of antileukemic therapy. Thus, the present invention identifies the transcriptional repressive ability of X-retinoic acid receptor-α proteins as the main leukemogenic mechanism in APL and implicate for the first time nuclear receptor co-repressors and histone deacetylases in the pathogenesis of human cancer.

The present invention demonstrates that one can treat tumors using specific inhibitors of histone deacetylases. For example, in one embodiment, one can treat a cancer caused in part by repression by a transcription factor by overcoming the transcriptional repression using specific inhibitors of histone deacetylases alone or in combination with retinoic acid receptor-α or other anti-neoplastic compounds. One example of such a tumor is non-Hodgkin's lymphoma although this type of therapy would be useful in treating various types of tumors even those without aberrant transcriptional repression. Further, the methods of the present invention can be used to overcome X-retinoic acid receptor-α transcriptional repression and concomitantly induce the retinoic acid dependent transactivation of retinoic acid target genes by retinoic acid receptor-α/Retinoid-X-Receptor-α and/or by X-retinoic acid receptor-α proteins themselves. The methods described herein can be used to induce terminal differentiation of tumor cells by targeting a specific transcription factor and specific transcriptional events.

The present invention is directed to a method of treating a tumor in an individual, comprising the step of administering to said individual a pharmacologically effective dose of an inhibitor of histone deacetylase. Further, the present invention is directed to a method of treating a tumor in an individual, comprising the step of administering to said individual a pharmacologically effective dose of a retinoid and an inhibitor of histone deacetylase.

The present invention is also directed to a method of treating APL in an individual, comprising the step of administering to said individual a pharmacologically effective dose of an inhibitor of histone deacetylase. The present invention is also directed to a method of treating APL in an individual, comprising the step of administering to said individual a pharmacologically effective dose of a retinoid and an inhibitor of histone deacetylase.

The present invention is also directed to a pharmaceutical composition, comprising a retinoid, an inhibitor of histone deacetylase and a pharmaceutically acceptable carrier.

The present invention is also directed to a method of antagonizing X-retinoic acid receptor-α transcriptional repression and concomitantly inducing the retinoic acid dependent transactivation of retinoic acid target genes by retinoic acid receptor-α/retinoid-X-receptor-α and/or by X-retinoic acid receptor-α proteins themselves.

Generally, any retinoid, e.g., retinoic acid compound would be useful in the methods of the present invention if administered in a pharmacologically effective dose. Representative examples of retinoid compounds useful in the methods of the present invention include all-trans-retinoic acid, 4-hydroxy-retinoic acid, 9-cis retinoic acid, (E)-4-[2-(5,6,7,8-tetrahydro-2-naphtalenyl)-1-propenyl]-benzoic acid, 3-methyl-(E)-4-[2-(5,6,7,8-tetrahydro-2-naphtalenyl)-1-propenyl]-benzoic acid and 13-cis-retinoic acid. Preferably, the retinoic acid is administered in a dose of from about 1.5 mg/kg to about 7.5 mg/kg. Dosages and treatment schedules for other retinoic acid compounds are well known to those having ordinary skill in this art.

Generally, an inhibitor of histone deacetylase would be effective in the methods of the present invention if administered in a pharmacologically effective dose. Preferably, the inhibitor of histone deacetylase is selected from the group consisting of trichostatin A, trapoxin, sodium butyrate, apicidin, sodium phenylbutyrate, phenylacetate and 3-bromopropionate. For example, trichostatin A would be effective if administered in a dose of from about 10 ng/g body weight to about 1 mg/g body weight. Dosages and treatment schedules for other inhibitors of histone deacetylase are readily attainable by routine experimentation to those having ordinary skill in this art.

The present invention is also directed to a method of inducing differentiation of tumor cells in a tumor in an individual in need of such treatment, comprising the step of administering to said individual a pharmacologically effective dose of an inhibitor of histone deacetylase. Further, the present invention is also directed to a method of inducing differentiation of tumor cells in a tumor in an individual in need of such treatment, comprising the step of administering to said individual a pharmacologically effective dose of a retinoic acid and an inhibitor of histone deacetylase. Representative examples of tumors having aberrant transcriptional repression in which differentiation of tumor cells using this method of the present invention include non-Hodgkin lymphomas and leukaemias.

The present invention is also directed to a method of treating APL in an individual, comprising the step of administering to said individual a pharmacologically effective dose of a retinoid, e.g., retinoic acid and sodium phenylbutyrate. Preferably, the retinoic acid is administered in a dose of from about 0.05 mg/kg to about 7.5 mg/kg. Representative examples of retinoic acids are listed above. Preferably, sodium phenylbutyrate is administered in a dose of from about 5 mg/kg body weight to about 1,000 mg/kg body weight.

The present invention is also directed to a method of treating a neoplastic disease in an individual, comprising the step of administering to said individual a pharmacologically effective dose of a retinoid and sodium phenylbutyrate. Dosages and representative retinoid are described above. Sodium phenylbutyrate is preferably administered in a dose of from about 5 mg/kg body weight to about 1,000 mg/kg body weight. Representative neoplastic diseases which can be treated using this method include leukemias, both acute and chronic leukemias, including APL and solid tumors such as neuroblastoma.

The following examples are given for the purpose of illustrating various embodiments of the invention and are not meant to limit the present invention in any fashion.

EXAMPLE 1
Plasmids and Antibodies

The following expression vector plasmids were utilized: pSG5-retinoic acid receptor-α, pSG5-PLZF, pSG5-promyelocytic leukaemia, pSG5-promyelocytic leukaemia-retinoic acid receptor-α, pSG5-PLZF-retinoic acid receptor-α[25] and pCEP4-N-CoR[53]. PLZF and retinoic acid receptor-α fusion proteins were cloned in pGEX-5X (Pharmacia Biotech.). For the immunofluorescence, the RPa (F) anti-retinoic acid receptor-α[54], the R18 anti-PLZF[30], and the anti-promyelocytic leukaemia[55] antibodies were provided by P. Chambon, by P. G. Pelicci, and by P. Freemont, respectively. For Western blot and immunoprecipitation the following antibodies were utilized: SMRT and anti-N-CoR Abs (Santa Cruz Biotech); RPa(F) anti-retinoic acid receptor-α; anti-promyelocytic leukaemia provided by M. Koken and H. de The[13]; and anti-PLZF[22].

EXAMPLE 2
Construction of the Transgene

A human Cathepsin-G (hCG) minigene expression vector was generated in order to drive the expression of human PLZF-retinoic acid receptor-α and promyelocytic leukaemia-retinoic acid receptor-α cDNA specifically in early stages of myeloid cell differentiation[32]. A blunt-ended 3 Kb EcoRI fragment spanning the PLZF-retinoic acid receptor-α fusion cDNA[30], was cloned into the artificial SalI site of the hCG vector, as for the promyelocytic leukaemia-retinoic acid receptor-α fusion cDNA[32]. Finally, BamHI-NotI fragments from these constructions were purified for egg injection as described[32].

EXAMPLE 3
DNA and RNA Analysis

Genomic DNA extracted from mouse tails were digested with EcoRE or HindIII and hybridized with probe CT, a 250 bp HindIII-XbaI hCG genomic fragment, and probe HS1, a 1 Kb hCG genomic fragment. A murine 2.3 Kb BamHI p53 cDNA probe was used to normalize and determine the number of copies of the transgene, as well as to distinguish between homozygous and heterozygous mice with the help of a Phosphorimager Densitometer (Bio-Rad). Total RNA was prepared from mouse bone marrow using the guanidium thiocyanate method[56]. RT-PCR was used to analyze the expression of the transgene using primers shown in FIG. 1C, which were previously described[32]. For Northern blot analysis, denatured total RNA (20 mg) was hybridized with the human retinoic acid receptor-α probe IT[57], or the human PLZF Aval probe 5'-A (see also FIG. 1) following standard procedures[58].

EXAMPLE 4
Competitive RT-PCR

Competitive RT-PCR was also used to quantitate and compare the expression of the transgene in DNAse I treated RNA extracted from bone marrow cells from sex and age (two months old) matched promyelocytic leukaemia-retinoic acid receptor-α and PLZF-retinoic acid receptor-α mice following amplification conditions previously described[32]. Two pairs of oligonucleotides [Rd and Cat(b) and F1 and B1: see reference 32] were utilized for the competitive nested-RT-PCR approach that span Cathepsin-G intron 1, thus allowing the plasmid containing the hCG-transgene, which has been utilized as competitor, to be distinguished from the processed cDNA. Serial dilutions of the competitor have been added to the PCR reactions.

EXAMPLE 5
Immunofluorescence

Cytospins of bone marrow and spleen cells were fixed with 4% paraformaldehyde for 10 minutes, and permeabilized and blocked with 0.3% Triton/10% goat serum/1% BSA/0.1M TBS for 40 minutes. The cells were subsequently incubated with anti-PLZF, anti-retinoic acid receptor-α, or anti-promyelocytic leukaemia antibodies at room temperature for 3 hours. A Texas-Red-conjugated IgG was used as a secondary antibody, and 4',6-diamidino-2-phenylindole (DAPI, Sigma) nuclear staining was also applied.

EXAMPLE 6
Follow-Up of Transgenic Mice

One group of mice were bled on a fortnightly basis, together with appropriate littermate controls of the same sex and age. Automated and differential counts as well as morphological analysis of PB cells were performed on each sample in order to monitor the incidence of leukaemia. In a second group, 4 transgenic mice from each line and 4 controls were sacrificed every two months, at 3, 5, 7, 9 etc. months of age, for gross and microscopic examination of all organs and in particular PB, bone marrow, spleen, lymph nodes and thymus. These organs and their cell populations were analyzed morphologically on touch prep, smears and cytospin preparations stained with Wright-Giemsa (see below). Sixty nontransgenic (W.T.) and all the transgenic mice from two hCG-PLZF-retinoic acid receptor-α lines (5814, 6062), and from two hCO-promyelocytic leukaemia-retinoic acid receptor-α lines (6179, 6380), were followed-up. A Kaplan-Meyer plot for leukaemia-free survival was generated using StatView 4.5 for Macintosh.

EXAMPLE 7
Hematology, Histopathology and Immunohistochemistry

Mice were bled from the tail. WBC, hemoglobin (Hb) and platelet (Plt) counts in peripheral blood were determined with an automated counter (Technicon H2). Differential counts of peripheral blood and bone marrow were performed microscopically on Wright-Giemsa staining smears according to hematological standards. Post-mortem pathological examination was performed according to standard procedures. Sections (4 mm) from various organs, including bone marrow, spleen, liver, thymus and lymph nodes, were stained with hematoxylin and eosin and examined. Myeloperoxidase (MPO; Dako), Mac-2, B220/CD45R and CD3 antibodies (PharMingen) were used for the immunohistochemistry staining on bone marrow and spleen sections[32].

EXAMPLE 8
Flow Cytometry

Peripheral blood, bone marrow and spleen cells were incubated with fluorescence-conjugated Mac-1 (CD11b), Gr-1 (myeloid differentiation antigen), CD34, c-kit (CD117) and Sca-1 antibodies at 4° C. for 30 minutes after being blocked with an unlabeled CD16/32 antibody to block non-antigen-specific binding of antibodies to the murine FcgII/III receptors. Fluorescein isothiocyanate (FITC) o r phycoerythrin (PE) conjugated isotypic antibodies were used as a background control. Antibodies were obtained from PharMingen. Red blood cells were lysed with FACS lysing solution (Becton-Dickinson). Dead cells were gated out and at least $1 \times 10^4$ events were analyzed in each sample on a FACScan flow cytometer (Becton-Dickinson).

EXAMPLE 9
Leukaemia Transplantation

Bone marrow and spleen cells were collected from transgenic mice with overt leukaemia and wild type mice as controls. $2 \times 10^7$ bone marrow cells were subcutaneously injected into C57BL/6 and NIH Swiss nude mice (Jackson Lab., Bar Harbor), in triplicate immediately after collection. The recipient mice were followed up for tumor growth on the site of injection and for leukaemia development.

EXAMPLE 10
In Vivo AT-retinoic Acid Therapy

Retinoic acid clinical trials in hCG-X-retinoic acid receptor-α leukaemias (hCG-PLZF-retinoic acid receptor-α: transgenic lines 5814 and 6062; hCG-promyelocytic leukaemia-retinoic acid receptor-α transgenic lines 6179 and 6380[32]), was carried out as in human APL patients by administering all-trans-retinoic acid (ATretinoic acid) per os daily at a dose of 1.5 mg per gram of mouse body weight. The clinical trial with high doses of retinoic acid was carried out by administering 7.5 mg of AT-retinoic acid per gram body weight by daily intraperitoneal injections. During this period of treatment, the mice were bled once a week and white blood cells, hemoglobin, platelet and differential counts were used to evaluate the response to retinoic acid therapy. Untreated control groups consisted of leukaemic mice from the same lines also bled once a week.

EXAMPLE 11
Recombinant Protein and Protein Interaction Assays

GST-PLZF and GST-retinoic acid receptor-α fusion proteins were produced from *E. coli* DH5α and purified with glutathione-Sepharose 4B beads and used as affinity matrices. Protein interaction assays were performed in NETN-buffer (20 mM Tris pH 8.0, 100 mM NaCl, 1 mM EDTA, 0.5% NP-40) at 4° C. for 60 minutes with gentle rocking. Beads were washed five times with H Buffer (20 mM Hepes pH 7.7, 50 mM KCl, 20% glycerol, 0.1% NP-40) and bounded proteins were eluted in SDS Sample buffer, separated by SDS-PAGE and visualized by Western Blotting.

EXAMPLE 12
Immunoprecipitation

Nuclear extracts were prepared from KG1 transfected cells as described previously[59]. For in vivo immunoprecipitation, nuclear extracts from transfected KG1 cells were incubated with 10 mg/ml of anti-retinoic acid receptor-α, anti-promyelocytic leukaemia or anti-PLZF in NETN buffer at 4° C. for 60 minutes in the presence or absence of various concentrations of ATretinoic acid. Immunocomplexes were isolated by incubation with protein A/G agarose, washed 5 times in H buffer, analyzed by SDS-PAGE and visualized by Western blotting.

EXAMPLE 13
Transfection Assays 293T cells and KG1 cells were transfected by calcium phosphate precipitation, and by electroporation as already described[25], and luciferase activity of each sample was normalized against internal control β-galactosidase activity[25]. Transfected cells were treated with retinoic acid and/or Trichostatin A for 36 hours.

EXAMPLE 14
Cell Culture, Proliferation, Apoptosis and Differentiation Studies

Differentiation was evaluated performing the nitroblue tetrazolium (NBT) assay and morphological differential count[32]. Proliferation of bone marrow cells was evaluated by measuring DNA synthesis quantitating incorporation of $^3$H-thymidine (Amersham). Bone marrow cells were plated at a density of $2 \times 10^6$ cells/ml and were pulsed with $^3$H-thymidine at a final concentration of 2.5 mCi/ml.

The effects of sodium phenylbutyrate (PB), both alone and in combination with all-trans retinoic acid (RA), were evaluated in studies of proliferation, apoptosis, and differentiation of cultured leukemia cells. NB4 cells, a line that stably carries the PML/RAR-α fusion protein of acute promyelocytic leukemia[71], were maintained in RPMI1640 medium, which was supplemented with 10% fetal bovine serum and 1% of penicillin-streptomycin, at 37° C. in 5% $CO_2$ atmosphere. Cultures were established at an initial density of $10^5$ cells/ml in the presence or absence of drugs at various concentrations. Cellular proliferation was measured by assessment of $^3$H-thymidine incorporation. Aliquots (180 μl) from each culture were placed into 96-well plates in triplicate after 20 hrs of incubation, and 0.5 μCi of $^3$H-thymidine in 20 μl of medium was added to each well. After further incubation for 24 hrs, cells were harvested onto glass fiber filters (Wallac) and placed in a liquid scintillation counter (Wallac, 1450 microbeta Plus). The proportion of cells undergoing apoptosis was determined by Annexin V staining[72]. Aliquots (1 ml) from each culture were harvested after 48 hrs incubation and the cells were stained with fluorescein isothiocyanate (FITC)-conjugated Annexin V and propidium iodide, according to the manufacturer's instructions (PharMingen, San Diego, Calif.). Annexin V and propidium iodide positivity were analyzed by flow cytometry (Becton-Dickinson, Mountainview, Calif.). Cell viability was measured after 4 days of incubation by using trypan blue exclusion. Cellular differentiation was evaluated at day 4 of incubation using both an assay for nitroblue tetrazolium (NBT) reduction and expression of CD11b (a cell surface differentiation antigen)[73]. Briefly, $10^6$ cells were harvested and incubated with 0.1% NBT solution in the presence of 12-o-tetradecanoylphorbol 13-acetate (TPA) (0.1 μg/ml) for 1 hr. The pellet of the mixture was then resuspended with 0.04 M HCl/10% SDS and kept at room temperature for 24 hrs. The optical density was measured at 540 nm. For CD11b expression, $10^6$ cells were incubated with FITC-conjugated CD11b monoclonal antibody (PharMingen). A FITC-conjugated isotype was used as background control. Expression of CD11b, including percentage of positive cells and the fluorescence intensity, was determined by using flow cytometry (Becton Dickinson).

EXAMPLE 15
Immunofluorescence Staining and Western Analysis of Acetylated Histones Mononuclear cells from the patient's blood and bone marrow were isolated by density centrifugation and were applied on slides by cytospin. The slides were fixed in 95% ethanol/5% acetic acid for 1 min, permeabilized and blocked in 10% goat serum/1% BSA/0.3% Triton X-100/PBS for 40 min. The slides were then incubated with anti-acetylated histone H4 antibody (Upstate Biotechnology, Inc., Lake Placid, N.Y.) for 1 hr. A Texas-red-conjugated IgG was used as a secondary antibody to reveal the positivity; staining with 4',6-diamidino-2-phenylindole (DAPI) was used to reveal nuclei.

Nuclei from separated blood and bone marrow mononuclear cells were isolated by lysis in buffer containing 10 mM Tris-HCl pH 6.5, 50 mM sodium bisulfite, 1% Triton X-100, 10 mM $MgCl_2$, 8.6% sucrose and Dounce homogenization. Histones were isolated by acid extraction[74]. Isolated histones (5 mg) were then separated on 15% SDS-PAGE minigels (Bio-Rad, Hercules, Calif.) and transferred to nitrocellulose (Schleicher and Schuell, Keene, N.H.). Hyperacetylated histones were detected by antibodies that specifically recognize the hyperacetylated forms of histone H4 and histone H3 (Upstate Biotechnology) and were visualized by chemiluminescence (Pierce, Rockford, Ill.). As a control for the amount of protein loading, parallel gels were stained with Coomassie blue.

EXAMPLE 16
Case Report and Clinical Study

The patient used for clinical study is a 13 year old female who was diagnosed with acute promyelocytic leukemia in 1994. She underwent induction chemotherapy with all-trans retinoic acid and attained complete remission the following month. After two courses of post-remission chemotherapy, she remained well until a relapse in November, 1995. She achieved a second remission with all-trans retinoic acid treatment and underwent an allogeneic bone marrow transplant using marrow obtained from her brother in March, 1996. She relapsed again in October, 1997, and at this time, her disease was resistant to all-trans retinoic acid. She then underwent three induction attempts with various types of cytotoxic chemotherapy, all of which were unsuccessful. Despite concurrent cavitary aspergillosis and disseminated *Varicella zoster* infection, she achieved a third remission after treatment with arsenic trioxide in January, 1998; however, she relapsed in April, 1998 at the end of her first post-remission treatment course with that drug. Details of her therapy are presented in Table 1.

At the time of this study, the patient was receiving a lipid formulation of Amphotericin B for recurrent pulmonary aspergillosis. She was restarted on oral all-trans retinoic acid at a dose of 45 mg/m$^2$/day in two divided doses. After the patient again proved to be clinically resistant, sodium phenylbutyrate (supplied by the Cancer Treatment Evaluation Program, NCI) was begun at a dose of 150 mg/kg intravenously twice per day. The phenylbutyrate infusions began shortly after each dose of all-trans retinoic acid and continued for 60 to 90 minutes. During the post-remission treatment course, blood specimens collected on heparin were serially obtained before and 2, 4, and 6 hrs following a 2-hour infusion of phenylbutyrate for determination of histone acetylation levels in leukocytes. Bone marrow was serially obtained before and during treatment for morphology, cytogenetics, histone acetylation, and RT-PCR analysis of PML/RAR-α mRNA[75]. Signed informed consent from the patient's mother and the patient's verbal assent were obtained, and the study was reviewed and approved in advance by the Memorial Sloan-Kettering Cancer Center's Institutional Review Board.

TABLE 1

Treatment previously received by the patient with acute promyelocytic leukemia

| Date | Treatment | Response |
| --- | --- | --- |
| Nov. '94 | All-trans retinoic acid | Complete remission |
| Jan. '95 | Daunorubicin/cytarabine | " |
| Feb. '95 | Daunorubicin/cytarabine | " |
| Nov. '95 | | Relapse |
| Nov. '95 | All-trans retinoic acid | Complete remission |
| Mar. '96 | Allogeneic bone marrow transplant | " |
| Oct. '97 | | Relapse |
| Oct. '97 | All-trans retinoic acid | Progression |
| Nov. '97 | High-dose cytarabine/ L-asparaginase | Progression |
| Nov. '97 | 2-chlorodeoxyadenosine/ etoposide | Progression |
| Jan. '98 | Paclitaxel | Progression |

TABLE 1-continued

Treatment previously received by the patient with acute promyelocytic leukemia

| Date | Treatment | Response |
| --- | --- | --- |
| Jan. '98 | Arsenic trioxide | Complete remission |
| Apr. '98 | | Relapse |
| Apr. '98 | All-trans retinoic acid | Progression |

EXAMPLE 17
Generation of X-retinoic Acid Receptor Transgenic Mice

Figure 1B:
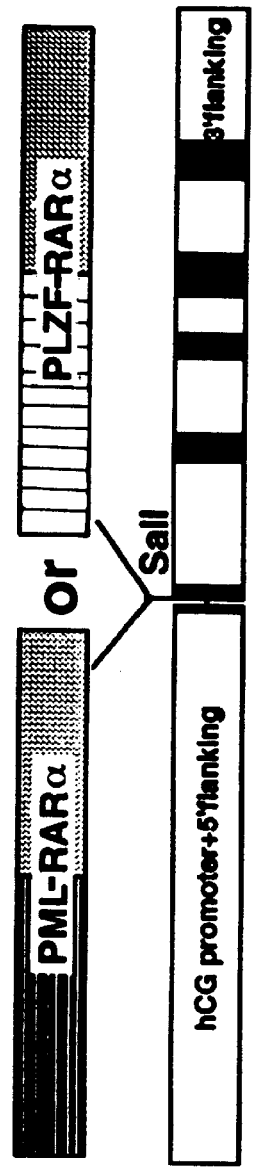
FIG. 1B shows a schematic representation of promyelocytic leukaemia-retinoic acid receptor-α and PLZF-retinoic acid receptor-α fusion cDNAs and the hCG minigene expression vector. The exons of the hCG gene are designated as solid boxes. The promoter and the 5' flanking region, as well as the 3' flanking region of the hCG gene are indicated. The X-retinoic acid receptor-α cDNAs were cloned into the hCG exon 1 into the artificial SalI site.
Figure 1C:
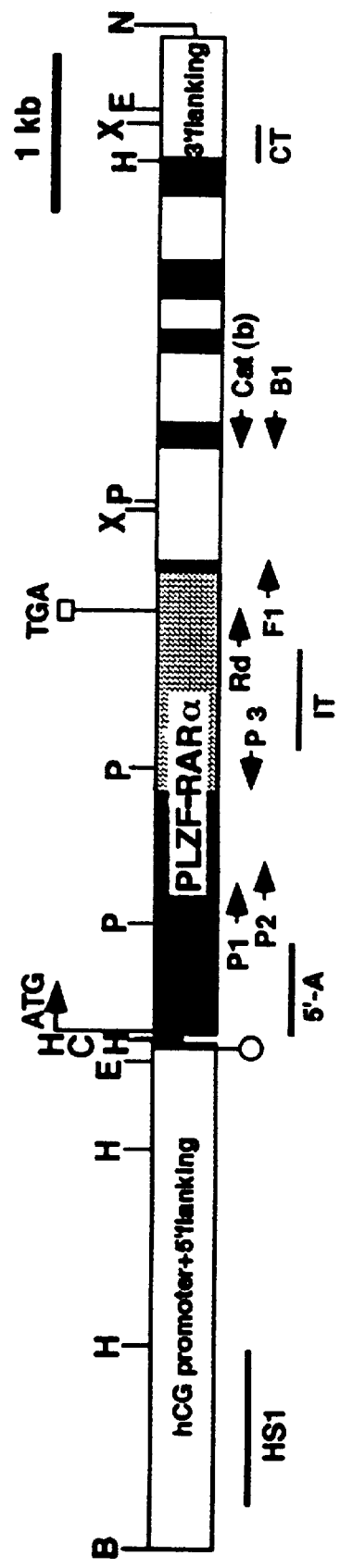
FIG. 1C shows the structure of the hCG-PLZF-retinoic acid receptor-α fragment utilized for injection. Restriction endonuclease sites are as follows: N, NotI; B, BamHI; E, EcoRI; C, ClaI; S, SalI; P, PMlI; X, XbaI; H, HindIII. The location of probes for Southern blot and primers for RT-PCR are shown underneath the structure of the injected fragment.
Figure 1D:
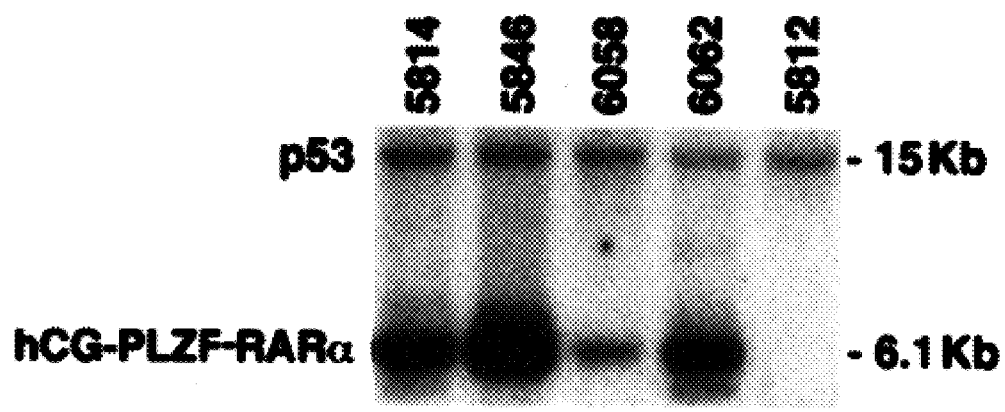
FIG. 1D shows a Southern blot of mouse genomic tail DNA from the four transgenic founders and 1 control digested with EcoRI and hybridized with probe CT reveals the expected bands of 6.1 Kb. A murine p53 cDNA fragment was used as an internal control probe to normalize DNA loading by cohybridization. The 15 Kb band identified by this probe is indicated. Lanes: 5814, 5846, 6058 and 6062, four founders; 5812, nontransgenic mouse.

To understand the role of promyelocytic leukaemia-retinoic acid receptor-α and PLZF-retinoic acid receptor-α (FIG. 1A) in leukaemogenesis and in mediating responses to retinoic acid, transgenic mice were generated in which the expression of the two chimeric cDNAs were under the control of a myeloid-promyelocytic specific human Cathepsin-G (hCG) minigene (FIGS. 1B and 1C). The generation of hCG-promyelocytic leukaemia-retinoic acid receptor-α transgenic mice has been described[32]. The PLZF-retinoic acid receptor cDNA was subcloned into the 5' untranslated portion from exon 1 of the hCG gene utilizing a unique SalI restriction enzyme cloning site which was introduced just upstream the hCG ATG which was previously mutagenized (FIGS. 1B and 1C). The progeny obtained from injection of the hCG-PLZF-retinoic acid receptor-α was screened by Southern blot utilizing a human specific Cathepsin-G probe (CT) (FIG. 1C). Four independent transgenic founders carrying the hCG-PLZF-retinoic acid receptor-α transgene (FIG. 1D) were identified, with two to fourteen intact copies of the transgene in a head to tail and/or tail to tail arrangement as evaluated by Southern blot analysis of offspring from the various founders carried out with two distinct probes (HS1 and CT), and two different restriction enzyme digestions (EcoRI and HindIII) (not shown).

Figure 1E:
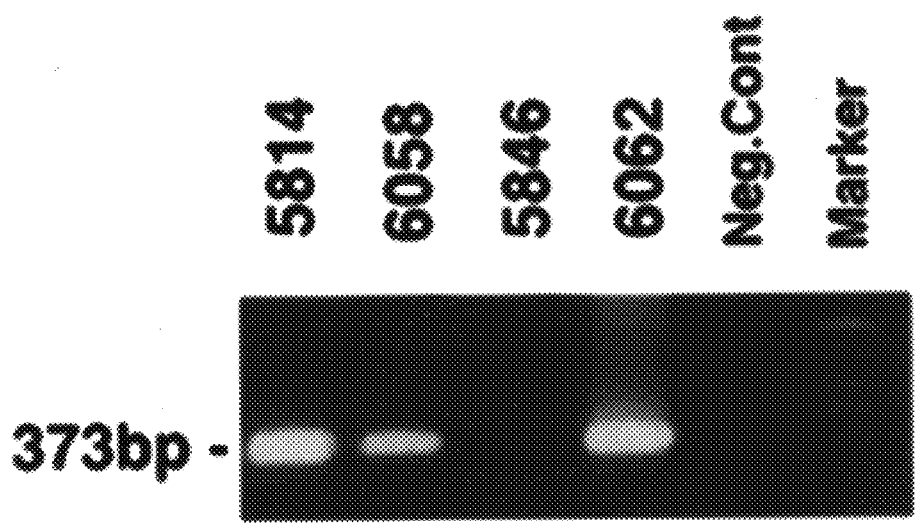
FIG. 1E shows a RT-PCR analysis of hCG-PLZF-retinoic acid receptor-α fusion mRNA expression in bone marrow cells from progeny of each founder. Representative results of nested RT-PCR utilizing two pairs of oligonucleotides [Rd and Cat(b) and F1 and B1] is shown: negative control, RNA from a nontransgenic mouse; marker, pGEM DNA marker (Promega). Line 5846, despite the integration of a high copy number of the transgene, did not express the hCG-PLZF-retinoic acid receptor-α mRNA.
Figure 1F:
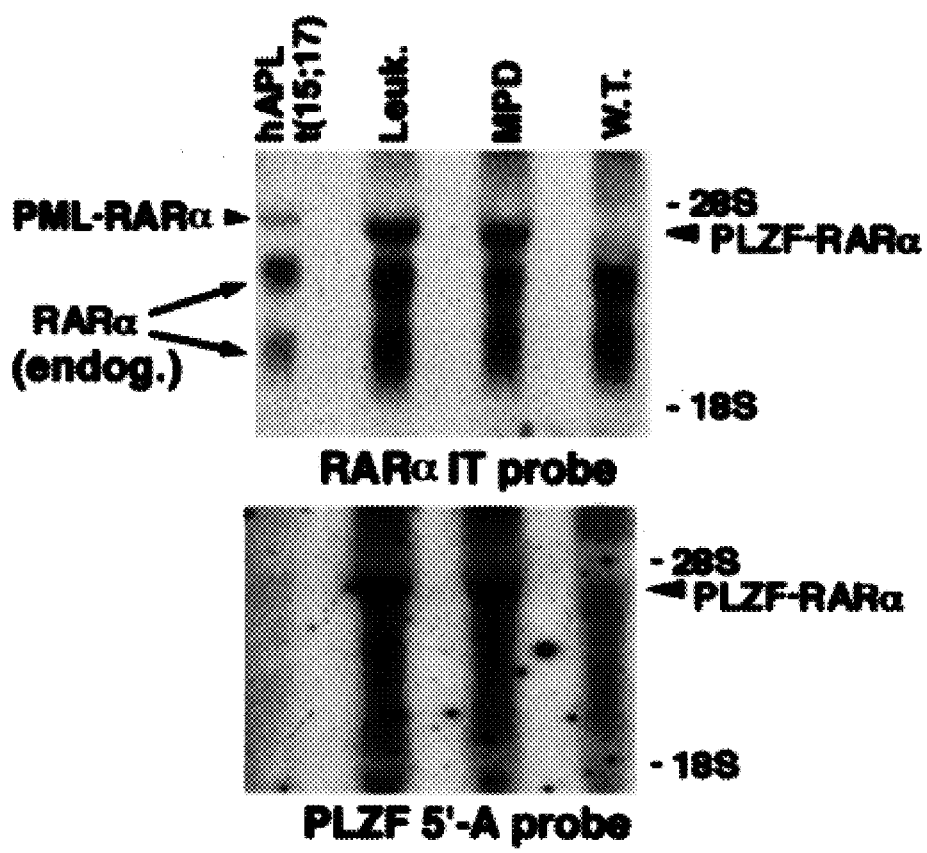
FIG. 1F shows a Northern blot on total RNA from PLZF-retinoic acid receptor-α transgenic mice with leukaemia (Leuk.) or myeloproliferative disorder (MPD) hybridized with the human retinoic acid receptor-α probe IT or the human PLZF probe 5'-A: W.T., nontransgenic mouse; hAcute promyelocytic leukaemia, APL patient with t(15; 17) (promyelocytic leukaemia-retinoic acid receptor-α of bcr-1 type[10]). The expected 3.9 Kb hCG-PLZF-retinoic acid receptor-α transcript (black right arrowhead), and the 4.4 Kb human promyelocytic leukaemia/retinoic acid receptor-α transcript (left black arrowhead) are indicated. The two endogenous murine retinoic acid receptor-α transcripts and the position of the 28S and the 18S ribosomal RNAs are also indicated.
Figure 1G:
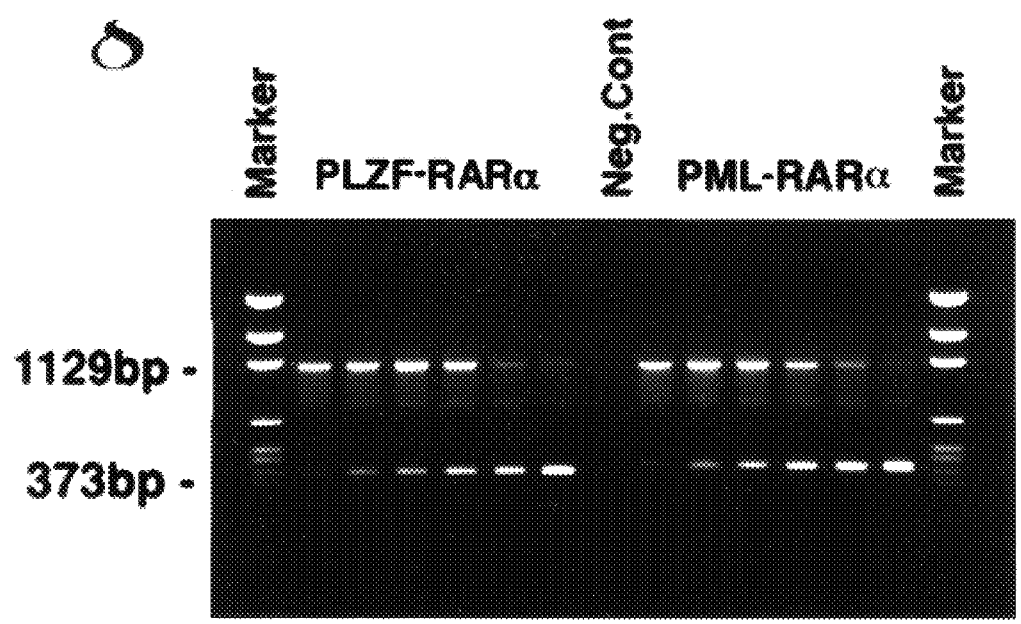
FIG. 1G shows a competitive RT-PCR indicating comparable expression of the transgene in DNAse I treated RNA extracted from bone marrow cells from sex and age (two months old) matched promyelocytic leukaemia-retinoic acid receptor-α and PLZF-retinoic acid receptor-α. A 373 bp fragment is amplified from processed hCG-X-retinoic acid receptor-α mRNAs, while a 1129 bp fragment is amplified from the competitor plasmid containing the hCG-PLZF-retinoic acid receptor-α transgene which includes hCG intron 1 (see also FIG. 1B,C). Serial dilutions of the competitor (from left to right: 1, 1:10, 1:20, 1:40, 1:80, 1:160), have been added to the PCR reactions performed with equal amounts of promyelocytic leukaemia-retinoic acid receptor-α or PLZF-retinoic acid receptor-α cDNAs. Negative control: no competitor and no cDNA was added. Marker, pGEM DNA marker (Promega).

The expression of the hCG-PLZF-retinoic acid receptor-α fusion gene was studied by RT-PCR analysis on RNA extracted from the bone marrow of the progeny of the various founders following a nested RT-PCR approach which utilizes two pairs of oligonucleotides [Rd and Cat(b) and F1 and B1] that span the hCG intron 1, which allowed the unprocessed gene to be distinguished from the processed cDNA (FIG. 1E). Progeny from three founders was found to express the transgene (FIG. 1E). Two lines (lines 5814 and 6062) were further expanded and characterized. The expression of the transgene was subsequently confirmed by Northern blot and immunofluorescence analysis on bone marrow samples obtained from mice which were in a pre-leukaemic-myeloproliferative phase or which had developed overt leukaemia (FIG. 1F). Northern blot analysis carried out with retinoic acid receptorα and PLZF probes confirmed the expression of a hCG-PLZF-retinoic acid receptor-α fusion transcript of the expected 3.9 Kb size in both transgenic lines. The levels of expression of promyelocytic leukaemia-retinoic acid receptor-α and PLZF-retinoic acid receptor-α in two of the four transgenic lines which were subsequently characterized and subjected to clinical trials with retinoic acid, were quantitated by competitive RT-PCR and were found to be comparable (FIG. 1G).

EXAMPLE 18
Nuclear Localization of Promyelocytic Leukaemia-Retinoic Acid Receptor-α and PLZF-Retinoic Acid Receptor-α Fusion Proteins in Bone Marrow Leukaemic Cells From Transgenic Mice In human APL, the presence of promyelocytic leukaemia-retinoic acid receptor-α results in the delocalization of promyelocytic leukaemia and PLZF from the nuclear bodies (Nbs), to microspeckled nuclear structures where the three proteins appear to colocalize[13]. Therefore, the nuclear localization of the promyelocytic leukaemia-retinoic acid receptor-α and the PLZF-retinoic acid receptor-α in bone marrow cells from transgenic mice was studied by immunofluorescence. In parallel, whether the presence of X-retinoic acid receptor-α proteins would result in an aberrant nuclear localization of promyelocytic leukaemia and/or PLZF was determined.

Figure 2:
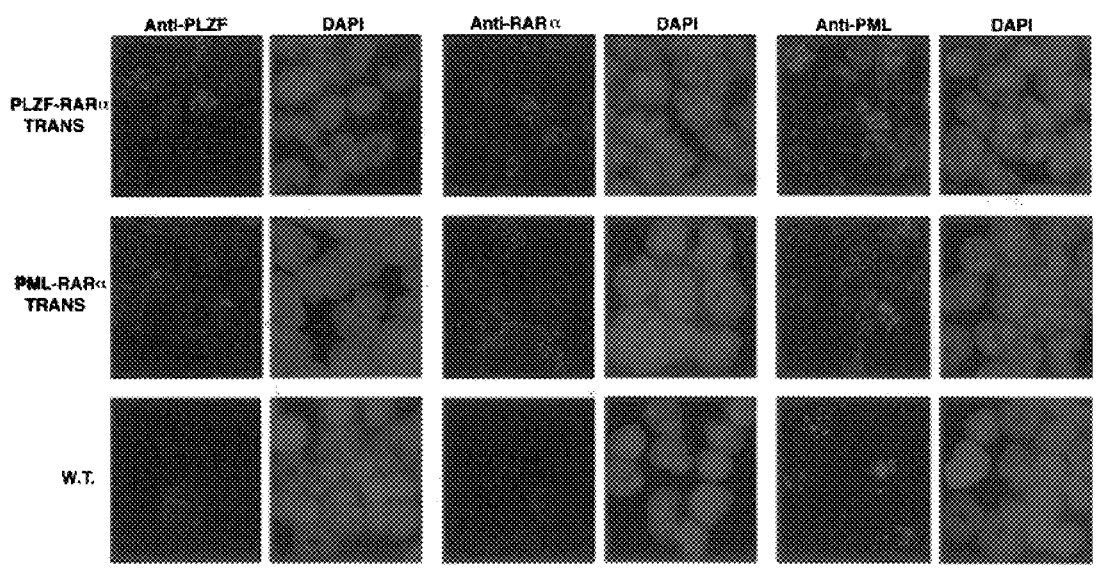
FIG. 2 shows that X-retinoic acid receptor-α proteins acquire a microspeckled nuclear distribution and delocalize promyelocytic leukaemia and PLZF proteins. Immunofluorescence staining of bone marrow cells from control mice (W.T.) and leukaemic hCG-X-retinoic acid receptor-α transgenic mice. In W.T. mice, promyelocytic leukaemia is localized within the nuclear bodies. PLZF and retinoic acid receptor-α staining is restricted to immature cells which display a diffused/microspeckled pattern (bottom panel). In promyelocytic leukaemia-retinoic acid receptor-α leukaemic cells, staining with anti-promyelocytic leukaemia, anti-PLZF and anti-retinoic acid receptor-α antibodies shows an indistinguishable microspeckled pattern (middle panel), supporting the notion that promyelocytic leukaemia-retinoic acid receptor-α can delocalize promyelocytic leukaemia and PLZF. In PLZF-retinoic acid receptor-α leukaemic cells, staining with anti-promyelocytic leukaemia, anti-PLZF and anti-retinoic acid receptor-α antibodies again shows a similar pattern, however unlike in promyelocytic leukaemia-retinoic acid receptor-α cells, the staining revealed a nuclear diffused distribution with the presence of fewer and larger microspeckles (top panel). Dapi staining was used to visualize cell nuclei.

Both the promyelocytic leukaemia-retinoic acid receptor-α and the PLZF-retinoic acid receptor-α showed a striking microspeckled/diffused nuclear localization pattern detectable with anti-promyelocytic leukaemia or anti-PLZF antibodies as well as with the anti-retinoic acid receptor-α antibody which recognizes the retinoic acid receptor-α portion retained in the X-retinoic acid receptor-α chimeras (FIG. 2). However, X-retinoic acid receptor-α proteins did not show an identical nuclear distribution in that PLZF-retinoic acid receptor-α accumulated in fewer, larger speckles and showed a more pronounced diffused nuclear distribution, while promyelocytic leukaemia-retinoic acid receptor accumulated in multiple microspeckles (FIG. 2). The endogenous promyelocytic leukaemia and PLZF proteins acquired a nuclear distribution indistinguishable from that of promyelocytic leukaemia-retinoic acid receptor-α or PLZF-retinoic acid receptor-α proteins (FIG. 2), which suggests that both fusion proteins can exhibit a dominant negative behavior upon the localization of promyelocytic leukaemia and PLZF proteins, and that both X-retinoic acid receptor-α proteins can form complexes with X proteins. These findings are consistent with the concept that promyelocytic leukaemia-retinoic acid receptor-α and PLZF-retinoic acid receptor-α form heterodimeric complexes with promyelocytic leukaemia and with PLZF respectively, and that promyelocytic leukaemia and PLZF interact with each other[13].

Figure 3A:
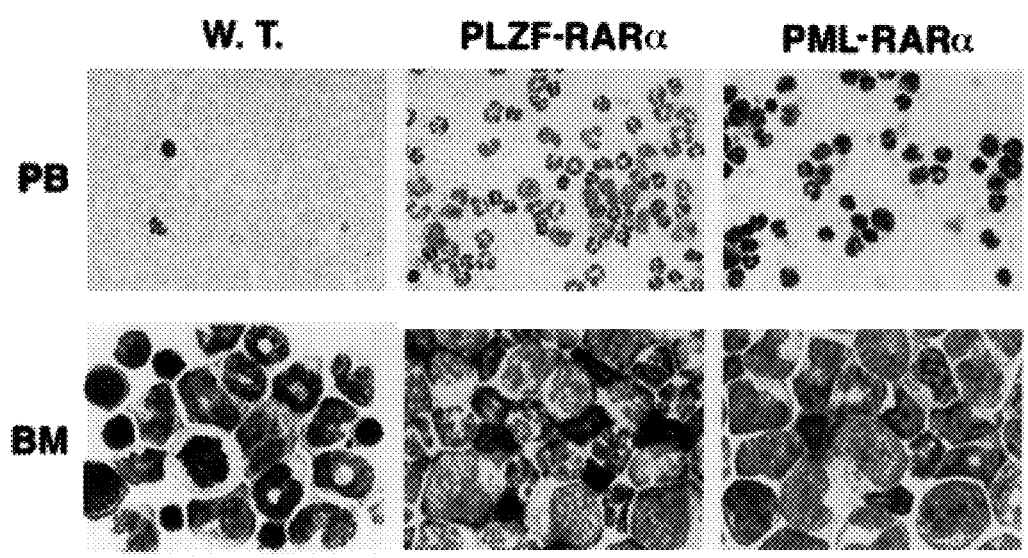
FIG. 3A and 3B shows a comparative analysis of morphology and cell surface markers in leukaemias from X-retinoic acid receptor-α transgenic mice. The smears of PB cells, or cytospins of bone marrow cells from control mice (W.T.), PLZF-retinoic acid receptor-α and promyelocytic leukaemia-retinoic acid receptor-α leukaemic mice were stained with Wright-Giemsa stain. Magnification: ×400 for PB; ×1000 for bone marrow. In the leukaemic mice the number of WBCs in the PB is dramatically increased. In the PLZF-retinoic acid receptor-α leukaemia the normal bone marrow cells, including erythrocytes, lymphocytes and megakaryocytes, are replaced by myeloid cells at various stages of maturation. In the promyelocytic leukaemia-retinoic acid receptor-α leukaemia the bone marrow is infiltrated by a more homogeneous population of cells made up of promyelocytes and myelocytes. Flow cytometric analysis on splenocytes from X-retinoic acid receptor-α leukaemic mice and control mice using antibodies against the cell surface markers Gr-1(PE-conjugated), Mac-1(FITC-conjugated), and C-Kit (PE-conjugated) is shown in the lower portion of the figure. The gating of all samples was set on the basis of the scatter pattern obtained with the isotypic control for each sample. In the histograms the isotypic control is shown by a dotted line. For each antibody, the percentage of positive cell populations is given in the respective quadrants and histograms. The Flow Cytometric analysis confirms that the leukaemic cell population in hCG-PLZF-retinoic acid receptor-α transgenic mice retains the ability to terminally mature as indicated by the marked accumulation of Gr-1$^+$/Mac-1$^+$ mature granulocytes and by a fewer number of c-Kit positive cells infiltrating the spleen.
Figure 3B:
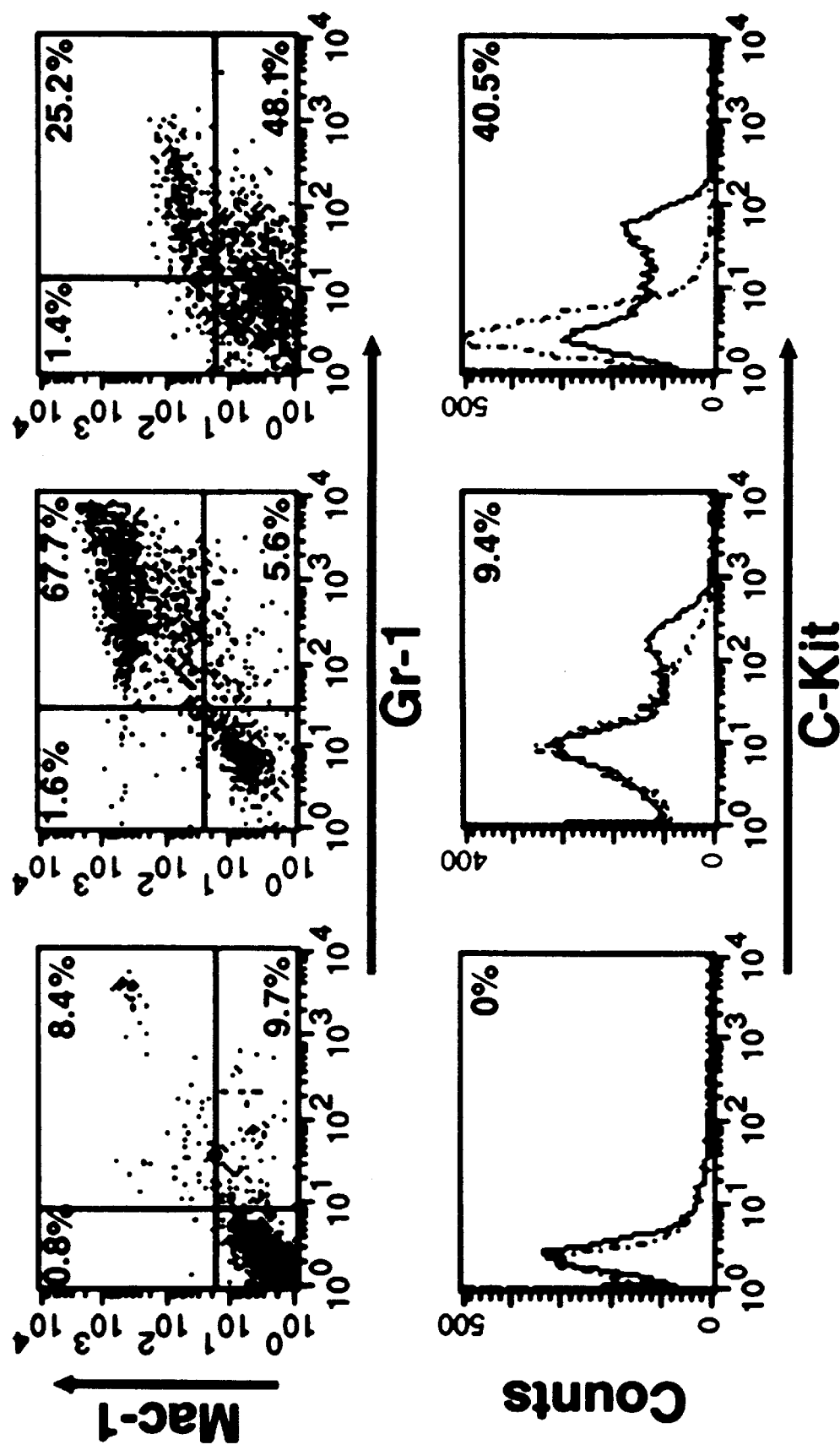

EXAMPLE 19
Myeloproliferative Disorder and Leukaemia in Promyelocytic Leukaemia-Retinoic Acid Receptor-α and PLZF-Retinoic Acid Receptor-α Transgenic Mice The generation of hCG-promyelocytic leukaemia-retinoic acid receptor-α and hCG-PLZF-retinoic acid receptor-α transgenic mice were used to examine the biological activity of the two X-retinoic acid receptor-α fusion proteins and to determine if they would cause an identical or different phenotype. Between 6 months and 1.5 years, all the hCG-PLZF-retinoic acid receptor-α transgenic mice from the two lines analyzed died of leukaemias, while only 25% of hCG-promyelocytic leukaemia-retinoic acid receptor-α mice developed leukaemias in the same time frame. Leukaemia in hCG-PLZF-retinoic acid receptor-α mice was characterized by a dramatic leukocytosis in the peripheral blood, and the infiltration in all organs by myeloid leukaemic progenitors with promyelocytic and myelocytic morphological features that fully retained the capacity to terminally mature, as revealed by differential counts on peripheral blood, bone marrow and spleen (FIGS. 3A and 3B). Thus, the leukaemia in hCG-PLZF-retinoic acid receptor-α mice resembled human chronic myeloid leukaemia (CML)[33], more than classical APL.

On the contrary, leukaemia in hCG-promyelocytic leukaemia-retinoic acid receptor-α mice was characterized by a more marked accumulation of immature blasts, and of cells blocked at the promyelocytic stage of differentiation which is distinctive of human APL (FIGS. 3A and 3B; Table 1 and reference 32). Immunohistochemistry and flow-cytometric analysis with antibodies for the cell surface markers c-Kit (totipotent stem cells and early myeloid progenitors), Gr-1 (various stages of granulocytes maturation and mature monocytes) and Mac-1 (mature monocytes and granulocytes), confirmed the myeloid nature of the leukaemias in hCG-X-retinoic acid receptor-α mice and their biological differences (FIG. 3 and not shown).

hCG-promyelocytic leukaemia-retinoic acid receptor-α leukaemia showed a significant accumulation of c-Kit positive cells in the spleen and bone marrow, which were otherwise negligible in hCG-PLZF-retinoic acid receptor-α leukaemia (in the spleen: W.T.=1.9%±1.9 (n=8); PLZF-retinoic acid receptor-α =4.0%±1.0 (n=4); promyelocytic leukaemia-retinoic acid receptor-α =14.7%±8.2 (n=6). p>0.03); in keeping with the fact that myeloid differentiation is impaired in hCG-promyelocytic leukaemia-retinoic acid receptor-α leukaemia, but can proceed to term in hCG-PLZF-retinoic acid receptor-α leukaemia. Subcutaneous injection of leukaemic bone marrow and splenic cells into nude mice demonstrated that both X-retinoic acid receptor-α leukaemias were transplantable (not shown). Hematological and pathological follow up of the hCG-PLZF-retinoic acid receptor-α transgenic mice, revealed that, as for the hCG-promyelocytic leukaemia-retinoic acid receptor-α transgenic mice[32], the leukaemia was preceded by a myeloproliferative disorder of variable duration. In this phase, myeloid precursors, retaining the ability to terminally differentiate into granulocytes, progressively accumulate in the bone marrow and the spleen, and in some cases the peripheral blood of hCG-PLZF-retinoic acid receptor-α mice, while in hCG-promyelocytic leukaemia-retinoic acid receptor-α mice the myeloproliferative disorder was characterized by the accumulation of immature myeloid cells and promyelocytes. Thus, both X-retinoic acid receptor-α proteins play a crucial role in APL pathogenesis and display overlapping but not identical biological and leukemogenic activities.

EXAMPLE 20
In Vivo Differential Response to Retinoic Acid Treatment in Promyelocytic Leukaemia-Retinoic Acid Receptor-α and PLZF-Retinoic Acid Receptor-α Transgenic Mice Whether X-retinoic acid receptor-α fusion proteins directly determined responses to retinoic acid was examined. To this end retinoic acid responses in vivo in leukaemias from hCG-X-retinoic acid receptor-α mice were compared by performing an in vivo therapeutic trial with retinoic acid at doses identical to those utilized for clinical trials in human APL. Leukaemic mice were identified by biweekly bleeding and retinoic acid treatment was initiated at the onset of leukaemia. Due to the inability to harvest bone marrow cells without sacrificing the animal, the response to retinoic acid was monitored by performing weekly differential and automated counts on peripheral blood, in order to examine white blood cell (WBC), platelet (Plt), red blood cell counts, hemoglobin (Hb) values, and to score for immature cells. The disappearance of immature cells from the peripheral blood, and the restoration of normal peripheral blood values with respect to wild-type controls were the criteria used to assess complete clinical remission. PML-retinoic acid receptor-α leukaemia responded well to retinoic acid with high remission rates (RR=80%) (FIG. 4).

Figure 4A:
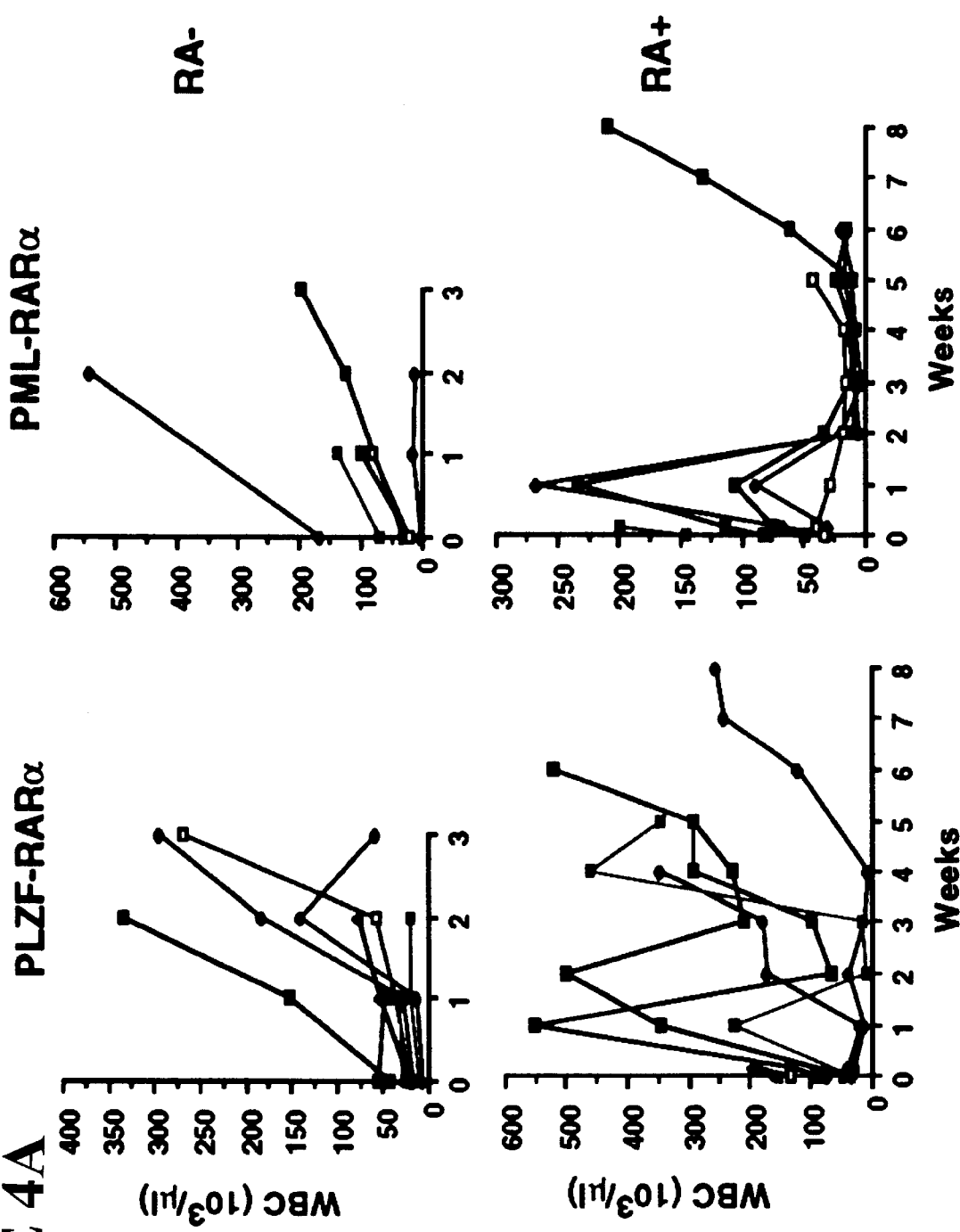
FIG. 4A illustrates white blood cell kinetics in untreated (retinoic acid−), or retinoic acid treated (retinoic acid+) PLZF-retinoic acid receptor-α (left panels) and promyelocytic leukaemia-retinoic acid receptor-α (right panels) leukaemic mice. Retinoic acid was administered per os daily at a dose of 1.5 mg per gram of mouse body weight.

In PML-retinoic acid receptor-α leukaemia, the kinetics of the white blood cell counts were similar to that observed in human APL patients upon retinoic acid treatment[34], namely a dramatic increase of white blood cells upon the first week of treatment followed by a decrease to normal values by the second and third week of treatment (FIG. 4A). This increase of white blood cells was due to the terminal maturation and concomitant mobilization of granulocytes from the bone marrow and the spleen to the peripheral blood induced by retinoic acid[34,35].

Figure 4B:
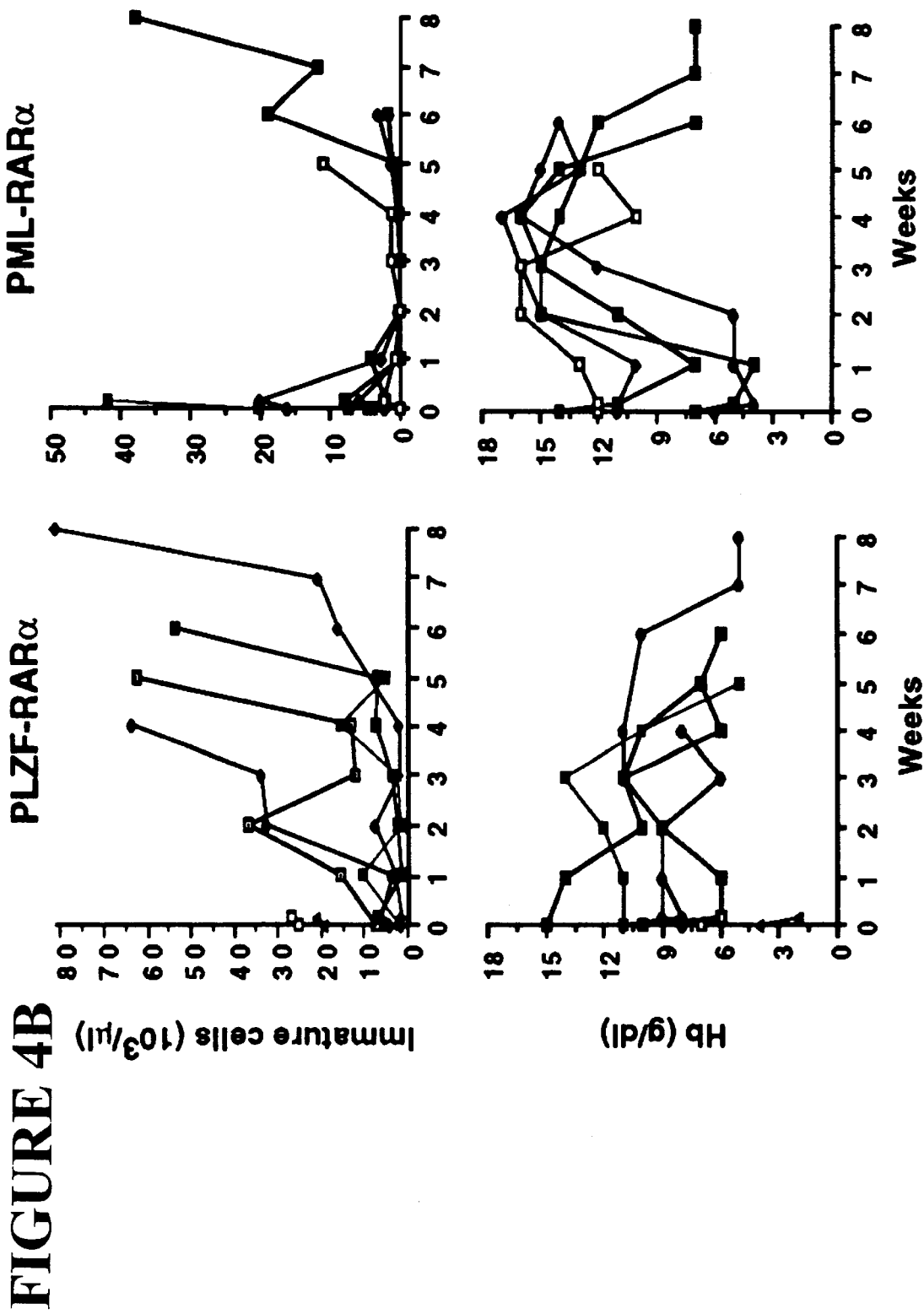
FIG. 4B shows kinetics of immature cells (blasts+promyelocytes+myelocytes) and hemoglobin (Hb) in PB in retinoic acid treated PLZF-retinoic acid receptor-α (left panels), and promyelocytic leukaemia-retinoic acid receptor-α (right panels) leukaemias. Without treatment, all transgenic mice died within 4 weeks from diagnosis. Retinoic acid prolonged survival of both promyelocytic leukaemia-retinoic acid receptor-α and PLZF-retinoic acid receptor-α transgenic mice up to eight week from diagnosis. However, in PLZF-retinoic acid receptor-α leukaemias, retinoic acid treatment never resulted in the normalization of all PB parameters, including WBC counts, Hb values, and the disappearance of immature cells from the PB. Clinical remission, on the contrary, was obtained by the third week of treatment in 80% of promyelocytic leukaemia-retinoic acid receptor transgenic mice.

In hCG-PML-retinoic acid receptor-α mice, remission was obtained by week three (FIG. 4). By contrast, PLZF-retinoic acid receptor-α leukaemia responded poorly to retinoic acid and complete remission was never achieved (FIG. 4). However, in both X-retinoic acid receptor-α leukaemias, retinoic acid prolonged survival, and induced hemopoietic differentiation, even if inefficiently as in the hCG-PLZF-retinoic acid receptor-α mice, as shown by the increase of white blood cells in PLZF-retinoic acid receptor-α leukaemia after one week of treatment. This was confirmed when retinoic acid induced differentiation in vitro and inhibited the growth of blasts from both X-retinoic acid receptor-α leukaemias (FIG. 4).

Upon retinoic acid treatment, peripheral blood profiles from human APL patients harboring t(11;17) showed an identical pattern of response with a comparable increase of white blood cell and partial cellular maturation. Similar to the PLZF-retinoic acid receptor-α transgenic mice, these patients never achieved complete remission[19,36,37]. Leukaemias in PML-retinoic acid receptor-α transgenic mice relapsed shortly after remission was achieved, were refractory to further retinoic acid treatment even at doses of retinoic acid five fold higher, and died within eight weeks of treatment (FIG. 4). Similarly, resistance to retinoic acid invariably occurred in human APL patients harboring t(15;17), when retinoic acid treatment was not accompanied by chemotherapy[18]. Thus, PML-retinoic acid receptor-α and PLZF-retinoic acid receptor-α fusion proteins play a direct role in determining responses to retinoic acid in APL, and leukaemia in PLZF-retinoic acid receptor-α transgenic mice are, as in human t(11;17) APLs, clinically resistant to retinoic acid.

EXAMPLE 21
PML-Retinoic Acid Receptor-α and PLZF-Retinoic Acid Receptor-α Are Transcriptional Repressors The refractory phenotype of t(11;17) APL to retinoic acid treatment could be due to the strong transcriptional repression function of the N-terminal portion of the PLZF protein, retained in the PLZF-retinoic acid receptor-α chimera, which contains a BTB/POZ domain capable of negatively regulating transcription[12,23]. Therefore, whether PLZF-retinoic acid receptor-α retained the dual transcriptional role of retinoic acid receptor-α was examined, i.e., its ability to repress and activate transcription in the absence or presence of retinoic acid, and compared its activity to that of PML-retinoic acid receptor-α. To this end, 293T cells were transfected with a reporter construct harboring a retinoic acid receptor responsive element (retinoic acid receptorE), and retinoic acid receptor, or PML-retinoic acid receptor-α, or PLZF-retinoic acid receptor-α expression vectors, and the ability of these proteins to repress or activate transcription with or without pharmacological doses of retinoic acid ($10^{-6}$ M) (FIG. 5) was evaluated.

Figure 5A:
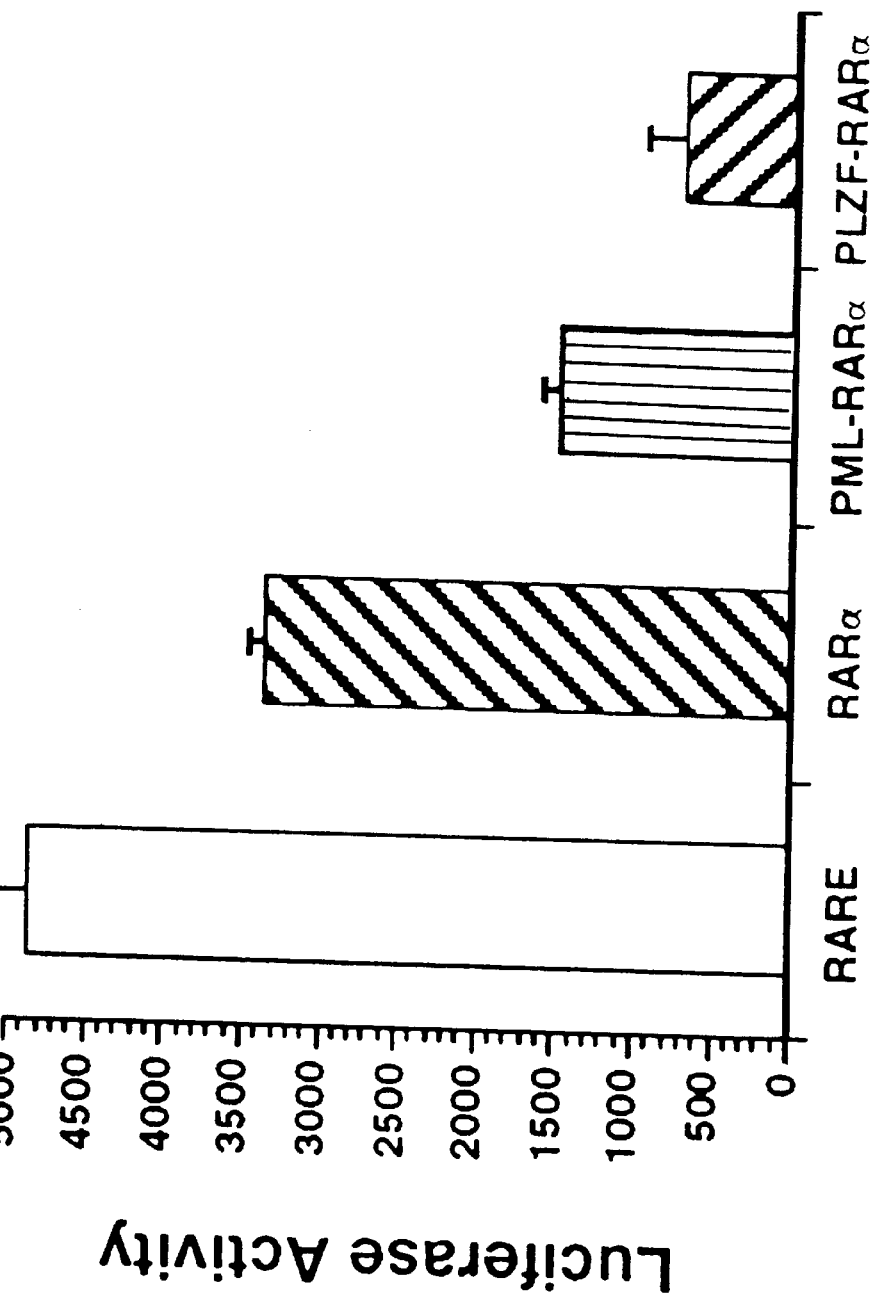
FIGS. 5A–5C show the transcriptional repression by promyelocytic leukaemia-retinoic acid receptor-α and PLZF-retinoic acid receptors-α. 293T cells were transfected with a 3Xretinoic acid receptorE-Luc reporter[52], 0.5 mg of CMV-b-galactosidase internal standard, and 0.5 mg of pSG5-retinoic acid receptor-α, pSG5-promyelocytic leukaemia-retinoic acid receptor-α or PLZF-retinoic acid receptor-α expression vectors (FIG. 5A) without retinoic acid (FIG. 5) with pharmacological doses of retinoic acid ($10^{-6}$ M). The experiment was performed in medium reconstituted with serum not depleted of endogenous retinoids. Luciferase activity was measured in a scintillation counter and normalized with the internal β-galactosidase standard. Values represent the averages of two independent transfections; no significant differences were observed between duplicate experiments. Both X-retinoic acid receptor-α proteins are potent transcriptional repressors in the absence of pharmacological doses of retinoic acid. At $10^{-6}$ M retinoic acid, a dose comparable to the hematic retinoic acid concentration obtained during in vivo retinoic acid treatment of APL patients, retinoic acid receptor-α and to a lesser extent promyelocytic leukaemia-retinoic acid receptor-α, can stimulate the transactivation of the reporter gene, while transactivation in the presence of PLZF-retinoic acid receptor-α is negligible. Note that in panels A and B luciferase activity is expressed by different scales.
Figure 5B:
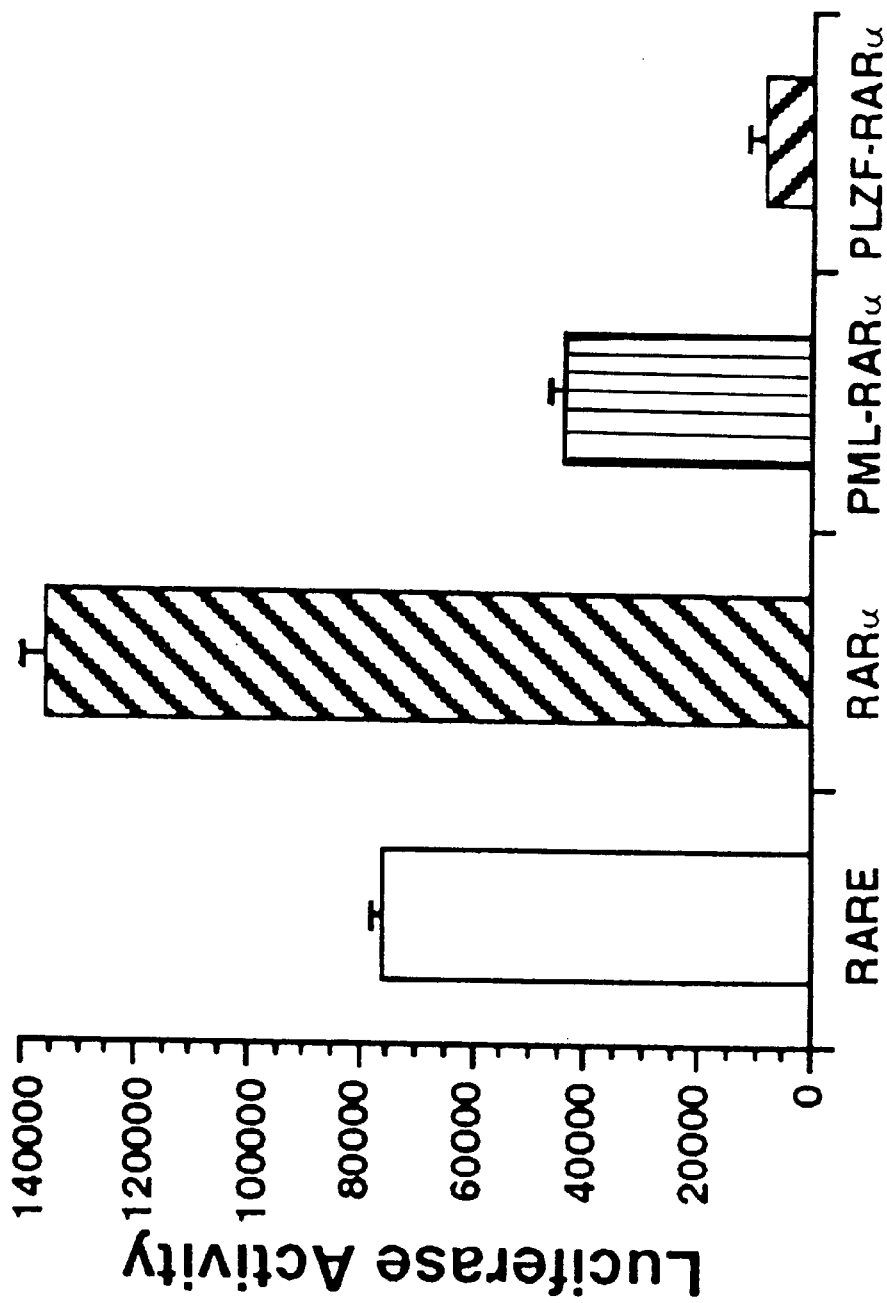
Figure 5C:
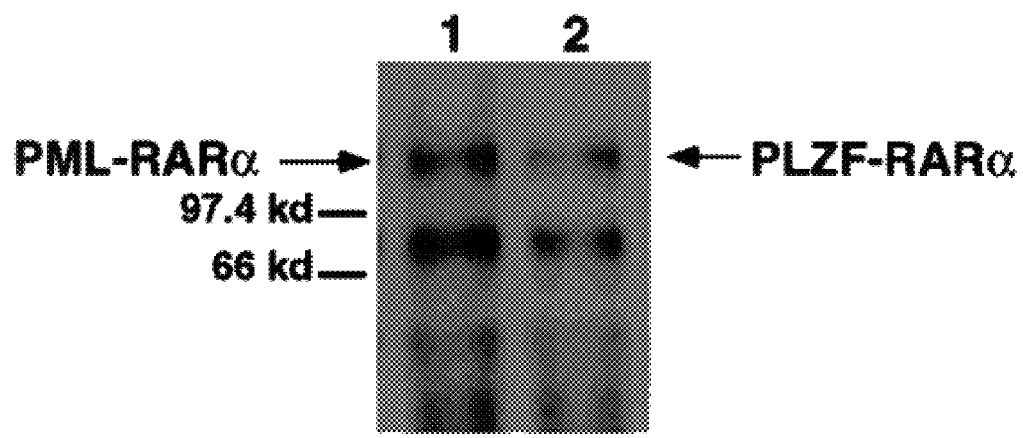

In comparison to the wild-type retinoic acid receptor-α, both PLZF-retinoic acid receptor-α and PML-retinoic acid receptor-α were more effective transcriptional repressors in the absence of pharmacological doses of retinoic acid (FIG. 5A), and were less potent activators in the presence of pharmacological concentrations of retinoic acid (FIG. 5B). In this respect, the PLZF-retinoic acid receptor-α chimera was consistently a stronger repressor and a much weaker activator compared to PML-retinoic acid receptor-α (FIG. 5). Thus, both X-retinoic acid receptor-α proteins can act as transcriptional repressors. However, pharmacological dose of retinoic acid can partially overcome PML-retinoic acid receptor-α, but not PLZF-retinoic acid receptor-α transcriptional repression.

EXAMPLE 22
Distinct Interactions of X-Retinoic Acid Receptor-α Proteins With Transcriptional Co-Repressors X-retinoic acid receptor-α proteins retain intact retinoic acid receptor-α DNA and ligand binding domains, and have an affinity for the ligand comparable to that of the wild-type retinoic acid receptor-[29,30]. Therefore, the inability of X-retinoic acid receptor to respond effectively to retinoic acid could result from a stronger association of the chimeric proteins with nuclear receptor co-repressors, such as SMRT and N-CoR. In order to show this, the sensitivity of such interactions to pharmacological concentrations of retinoic acid in co-immunoprecipitation experiments was examined.

Figure 6A:
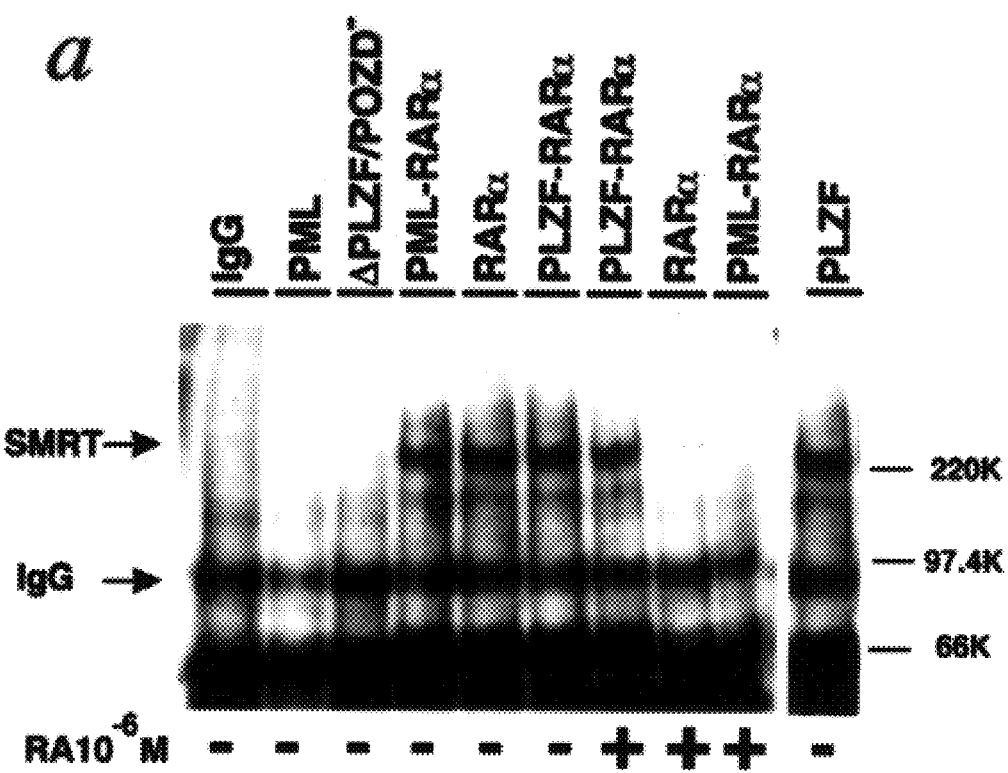
FIG. 6A shows that KG1 cells were transiently transfected with expression vectors encoding PLZF, promyelocytic leukaemia, retinoic acid receptor-α, promyelocytic leukaemia-retinoic acid receptor-α and PLZF-retinoic acid receptor-α and a truncated version of the PLZF protein lacking the POZ domain (DPLZF/POZD⁻). Nuclear extracts were obtained 2 days after transfection and used for co-immunoprecipitation of the endogenous SMRT protein (expressed at high levels in KG1 cells, data not shown) using an antibody to the retinoic acid receptor-α F region (retinoic acid receptor-α and retinoic acid receptor-α fusion proteins) or anti-promyelocytic leukaemia and anti-PLZF antibodies. Levels of expression of the transfected proteins were previously tested b y Western Blotting and normalized. The binding reaction was done in the presence or absence of retinoic acid for 1 hour. After immunoprecipitation, the complexes were resolved on a 5% SDS-PAGE gel. The gel was transferred to a solid support and Western blotted for SMRT with a SMRT antibody.
Figure 6B:
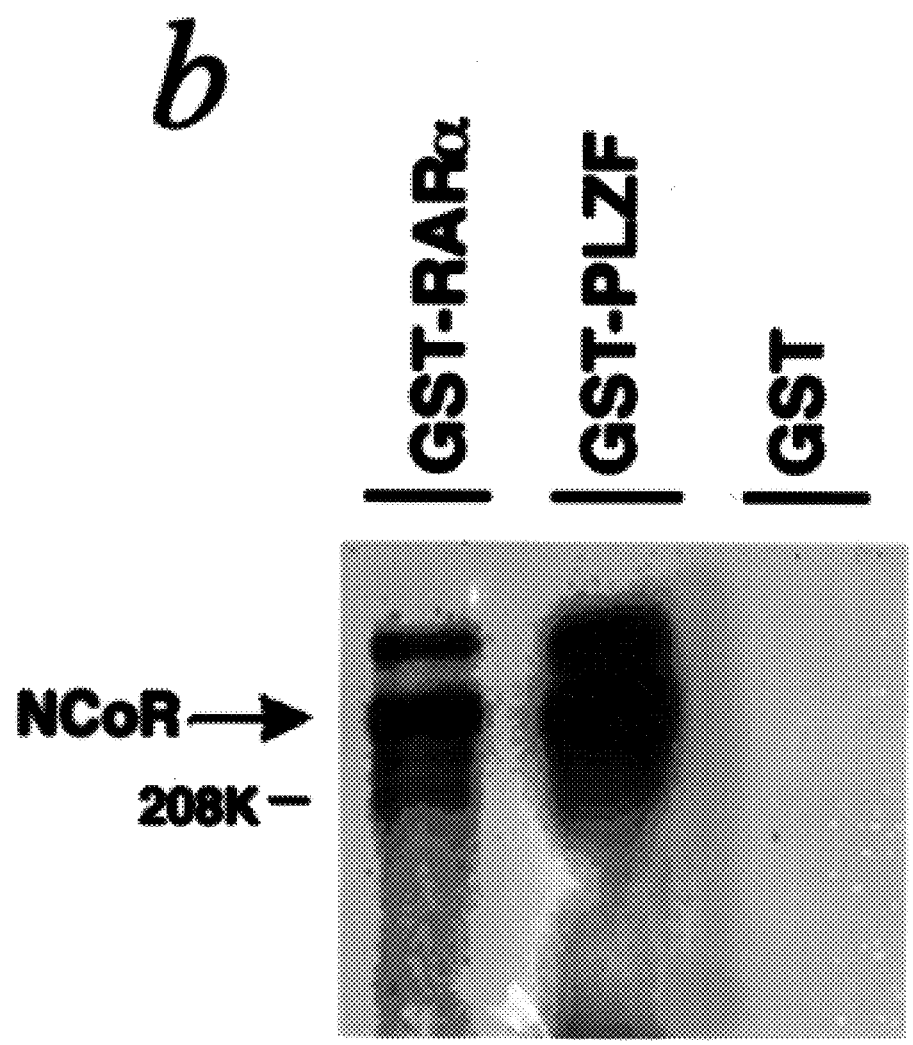
FIG. 6B shows the association of N-CoR with retinoic acid receptor-α and PLZF. KG1 cells were transiently transfected with N-CoR expression plasmids and nuclear extracts were prepared. The nuclear extracts were incubated with immobilized affinity matrices GST, GST-retinoic acid receptor-α and GST-PLZF and analyzed by SDS-PAGE together. The gel was transferred to a solid support and Western Blotted with a N-CoR antibody.

KG1 cells were transiently transfected with PLZF, PML, retinoic acid receptor-α, PML-retinoic acid receptor-α and PLZF-retinoic acid receptor-α expression vectors as well as with an expression vector encoding a truncated version of the PLZF protein lacking the POZ domain (DPLZF/POZD⁻). Transfected proteins were immunoprecipitated in the presence or the absence of $10^{-6}$ M retinoic acid, and co-immunoprecipitation of the endogenous SMRT protein was detected by Western blot (FIG. 6A). In extracts treated with retinoic acid, endogenous SMRT co-immunoprecipitated only with the PLZF-retinoic acid receptor-α chimeric protein, but not with the wild-type retinoic acid receptor-α or PML-retinoic acid receptor-α fusion protein (FIG. 6A). Furthermore, SMRT co-immunoprecipitated with the wild-type PLZF protein, but not with PML (FIG. 6A). The POZ domain of PLZF (aa1-120, see reference 9) was required for this association (FIG. 6A). In this respect it is worth noting that POZ-domain is also required for transcriptional repression by the PLZF protein[12]. Involvement of nuclear co-repressors in transcriptional repression by PLZF and PLZF-retinoic acid receptor-α is further supported by the ability of these proteins to associate with N-CoR (FIG. 6B). These results can, at least in part, explain the differential sensitivities of the two APL syndromes to retinoic acid and shed light on the mechanisms of transcriptional repression by the PLZF and PLZF-retinoic acid receptor-α proteins.

Figure 7A:
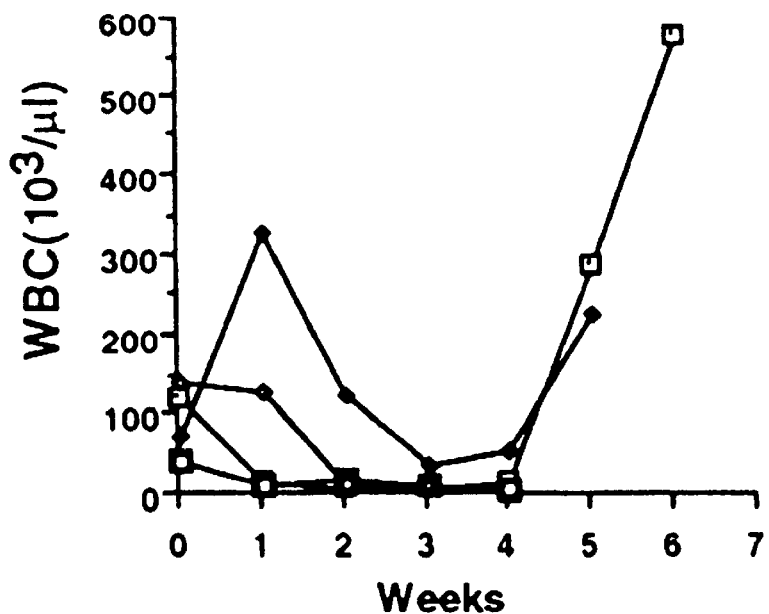
FIG. 7A shows white blood cell counts in leukaemic PLZF-retinoic acid receptor transgenic mice throughout retinoic acid treatment.
Figure 7B:
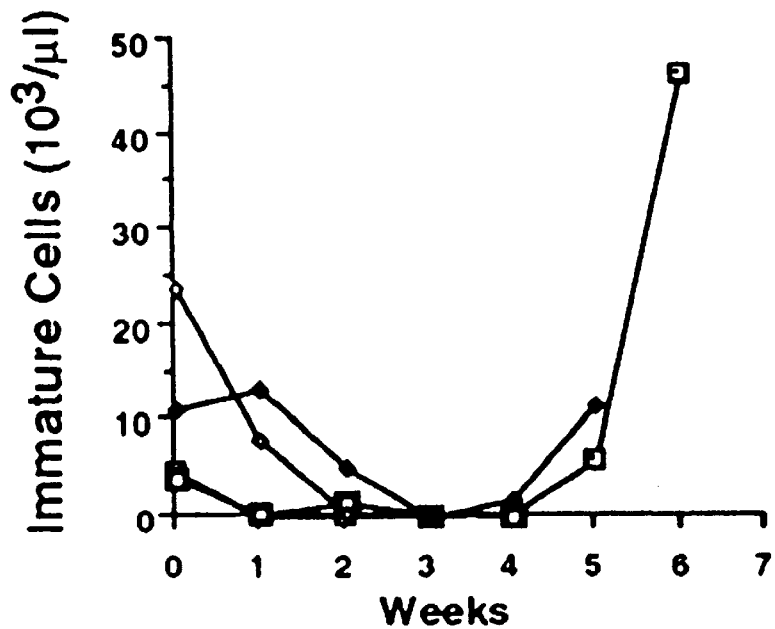
FIG. 7B shows absolute numbers of immature cells (blasts+promyelocytes+myelocytes) in leukaemic PLZF-retinoic acid receptor-α transgenic mice during retinoic acid treatment. In three out of four leukaemias remission was achieved by the third week of treatment, with a kinetics of response comparable to that observed in leukaemia from hCG-promyelocytic leukaemia-retinoic acid receptor-α mice subjected to treatment with lower doses of retinoic acid.
Figure 7C:
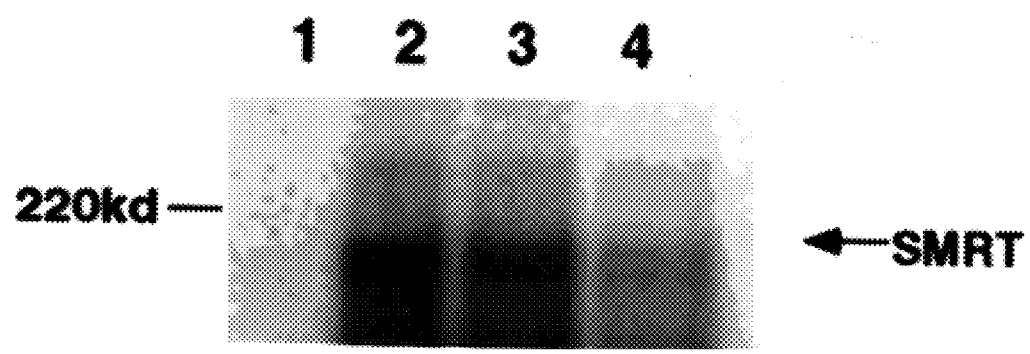
FIG. 7C shows that increasing retinoic acid concentrations dissociate PLZF-retinoic acid receptor-(X/SMRT co-repressor complex. KG1 cells were transiently transfected with a PLZF-retinoic acid receptor-α expression vector. Nuclear extracts were immunoprecipitated using an antibody to the retinoic acid receptor-α F region, and Western blotted with an anti-SMRT antibody in order to detect co-immunoprecipitating endogenous SMRT protein. The binding reaction was performed without retinoic acid (2), at $10^{-6}$ M (3), or $5 \times 10^{-5}$ M retinoic acid (4), for 1 hour at 4° C. In lane (1) the immunoprecipitation was performed without adding the anti-retinoic acid receptor-α antibody.

EXAMPLE 23
High Dose Retinoic Acid Treatment Causes Clinical Remission in PLZF-Retinoic Acid Receptor-α Transgenic Mice If the clinical irresponsiveness of leukaemias from hCG-PLZF-retinoic acid receptor-α transgenic mice to retinoic acid is due to an increased affinity of PLZF-retinoic acid receptor-α for nuclear co-repressors which retinoic acid cannot dissociate at either physiological and pharmacological doses, by further increasing the therapeutic dose of retinoic acid one could favor the dissociation of the PLZF-retinoic acid receptor-α/nuclear co-repressors complex releasing the dominant negative transcriptional repression exerted by this complex. Leukaemia from hCG-PLZF-retinoic acid receptor-α transgenic mice was treated therefore with a dose of retinoic acid five fold greater then the dose utilized for clinical trials in human APL. The response to retinoic acid was monitored as described above. PLZF-retinoic acid receptor-α leukaemia responded much better to a high dose of retinoic acid and clinical remission was obtained (RR=75%), as determined by the complete disappearance of immature cells from the peripheral blood, and the normalization of the peripheral blood parameters (FIGS. 7A and 7B). In keeping with this findings, increasing retinoic acid concentrations could dissociate, albeit not completely, the PLZF-retinoic acid receptor-α/SMRT co-repressor complex (FIG. 7C)

EXAMPLE 24

Trichostatin-A Overcomes X-Retinoic Acid Receptors Transcriptional Repression as Well as the Irresponsiveness of PLZF-Retinoic Acid Receptor-α Leukaemic Cells to Retinoic Acid Nuclear receptor co-repressors form complexes with histone deacetylases (HDAC1 or 2), resulting in nucleosome assembly and transcriptional repression[15]. To determine if histone deacetylases associated activity was required for transcriptional repression and the irresponsiveness to retinoic acid caused by X-retinoic acid receptor-α proteins, the effect of Trichostatin A (TSA), a specific inhibitor of histone deacetylases[31], on these functions was examined. 293T cells were transfected with the retinoic acid receptorE-Luc reporter construct and retinoic acid receptor-α, PML-retinoic acid receptor-α or PLZF-retinoic acid receptor-α expression vectors, and the ability of these proteins to activate transcription in the presence of Trichostatin A and retinoic acid was evaluated.

Figure 7D:
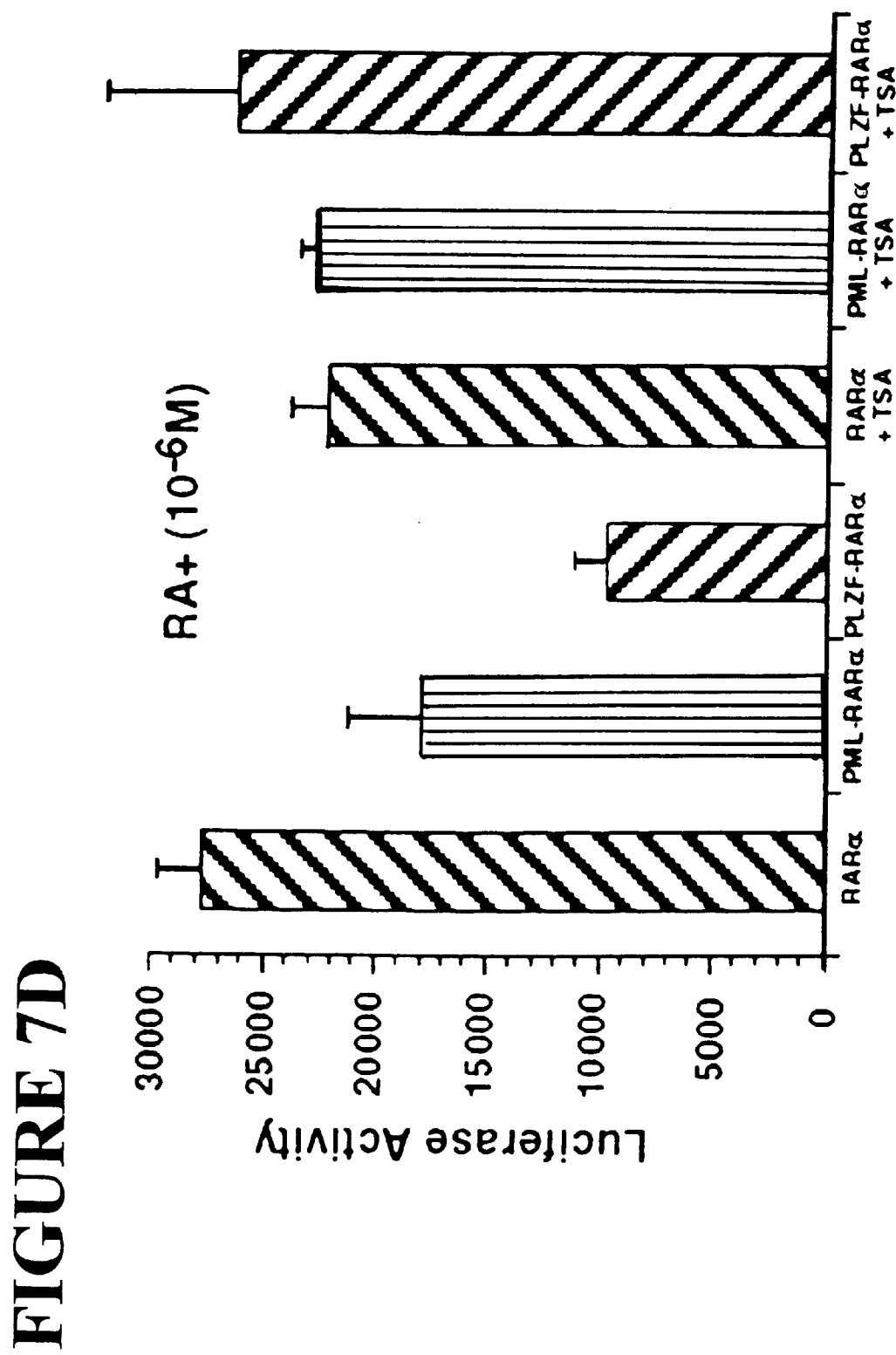
FIG. 7D shows that Trichostatin A reverts the transcriptional repression by X-retinoic acid receptor-α proteins. 293T cells were transfected with the 3Xretinoic acid receptor-αE-Luc reporter, CMV-β-galactosidase internal standard, and pSG5-retinoic acid receptor-α, pSG5-promyelocytic leukaemia-retinoic acid receptor-α or PLZF-retinoic acid receptor-α expression vectors with retinoic acid ($10^{-6}$ M), with or without Trichostatin A (150 nM). Luciferase activity was normalized with the internal β-galactosidase standard. Values represent the averages of two independent transfections. In the presence of retinoic acid and Trichostatin A, X-retinoic acid receptor proteins showed transactivation abilities indistinguishable form that of retinoic acid receptor-α, while Trichostatin A alone had negligible transcriptional effects (not shown).

Trichostatin A reverted the transcriptional repression of both X-retinoic acid receptor-α proteins (FIG. 7D). Whether trichostatin A overcomes retinoic acid irresponsiveness of bone marrow cells from PLZF-retinoic acid receptor-α leukaemic mice refractory to the in vivo retinoic acid treatment was shown. PLZF-retinoic acid receptor-α, leukaemic cells were treated with retinoic acid, trichostatin A and retinoic acid+trichostatin A, and inhibition of growth and induction of myeloid differentiation, the two main effects of retinoic acid treatment in APL, were evaluated by $^3$H-thymidine incorporation and NBT assays.

Figure 7E:
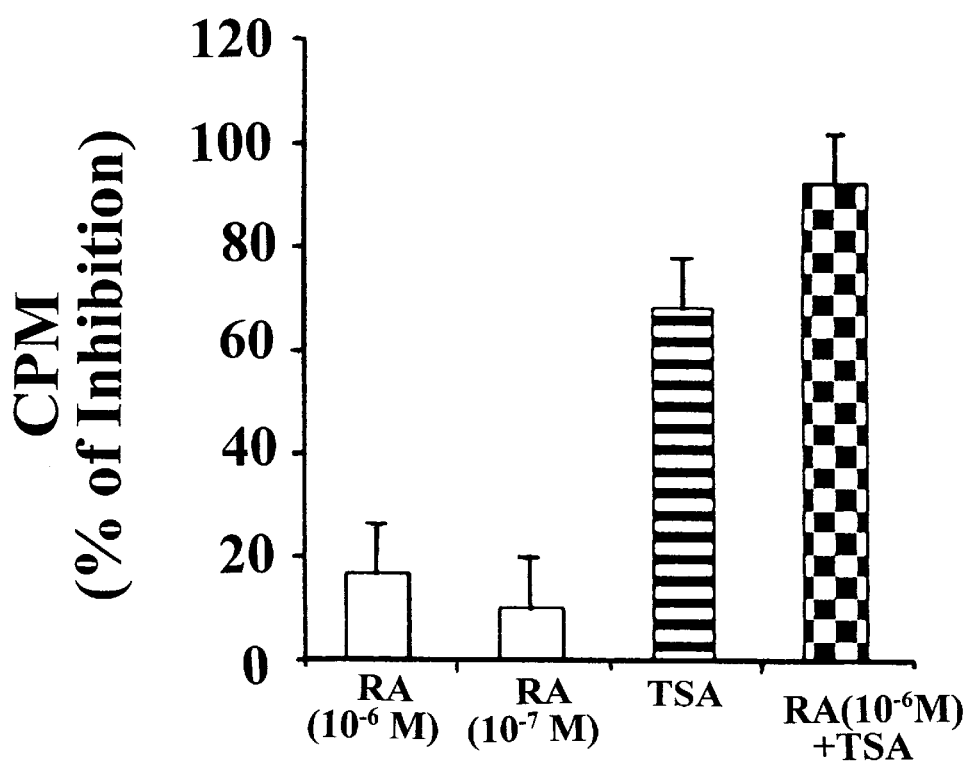
FIG. 7E and FIG. 7F show that Trichostatin A overcomes retinoic acid irresponsiveness of PLZF-retinoic acid receptor-α bone marrow leukaemic cells. Bone marrow cells were plated at density of 2'10$^6$ cells/ml with various concentrations of retinoic acid (10$^{-6}$ M; 10$^{-7}$ M), and/or Trichostatin A (5 ng/ml). Myeloid differentiation was evaluated by performing the nitroblue tetrazolium (NBT) assay, and cell proliferation by measuring DNA synthesis quantitating incorporation of $^3$H-thymidine. While retinoic acid induced little if no effects, retinoic acid and Trichostatin A, in combination, showed a dramatic growth inhibitory and differentiating activity.
Figure 7F:
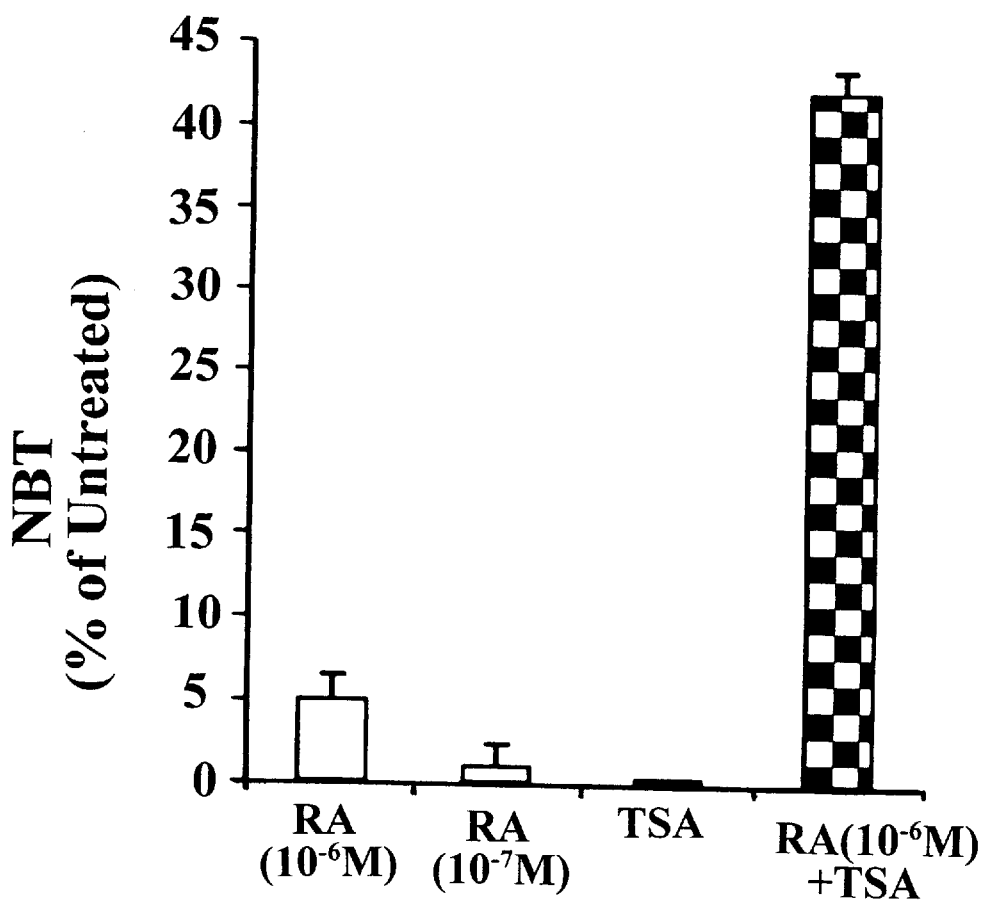
Figure 8A:
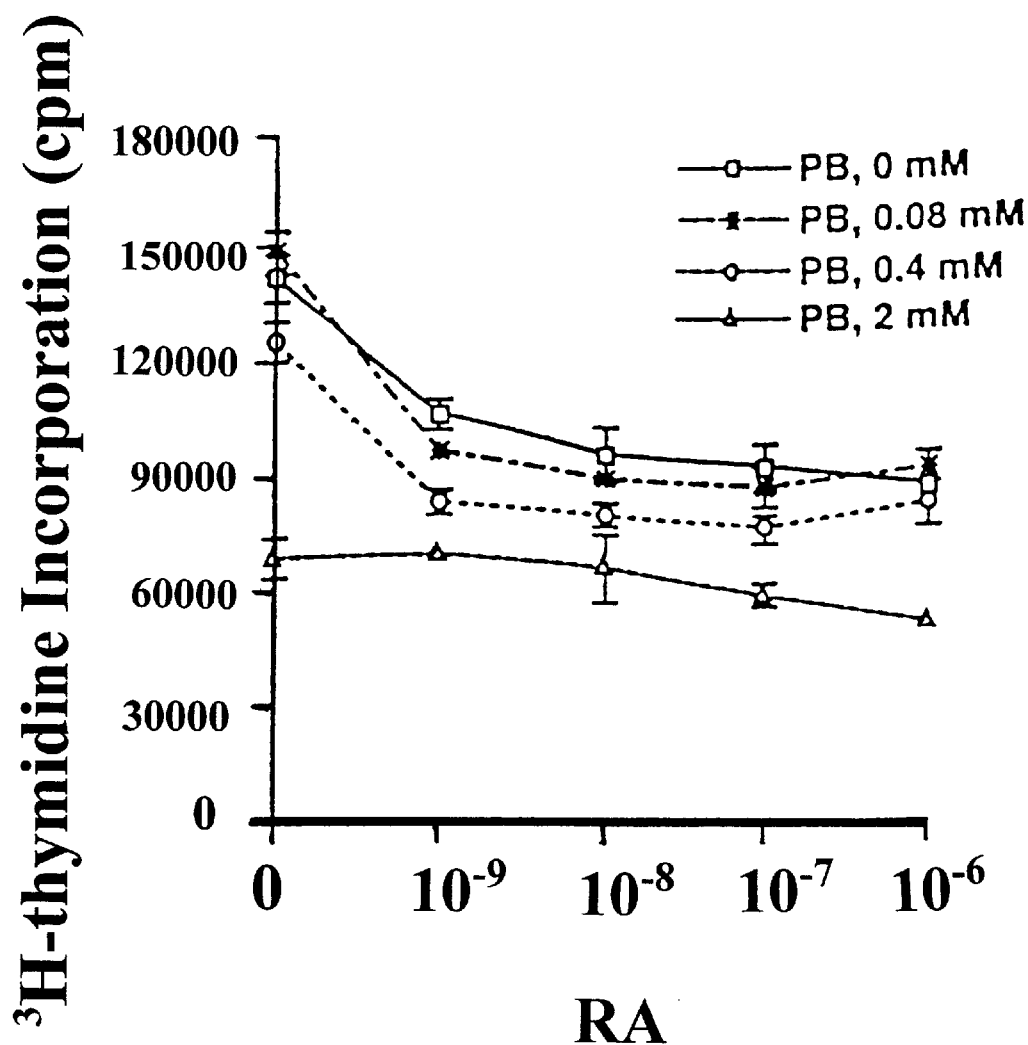
FIG. 8 shows the effects of sodium phenylbutyrate (PB) alone and in combination with all-trans retinoic acid (RA) on proliferation, apoptosis and differentiation of NB4 cells. Each point represents results from three experiments (mean±SD). Panel A shows the inhibition of proliferation of NB4 cells by PB and/or RA detected by $^3$H-thymidine incorporation. Panel B shows the percentage of apoptotic cells after 2 days of incubation using flow cytometric analysis of Annexin V. Panels C and D show the induction of differentiation after 4 days in culture as manifest by the median fluoresence intensity of cells expressing the maturation marker CD11b or reduction of nitroblue tetrazolium (NBT), respectively.
Figure 8B:
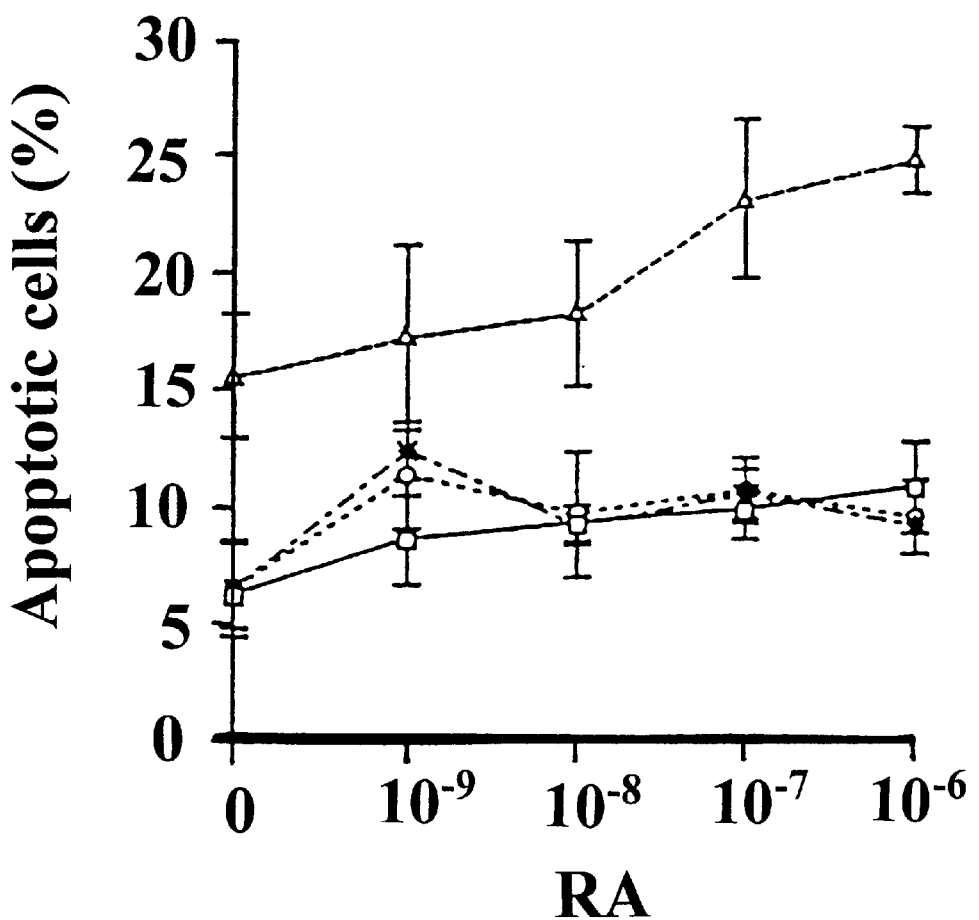
Figure 8C:
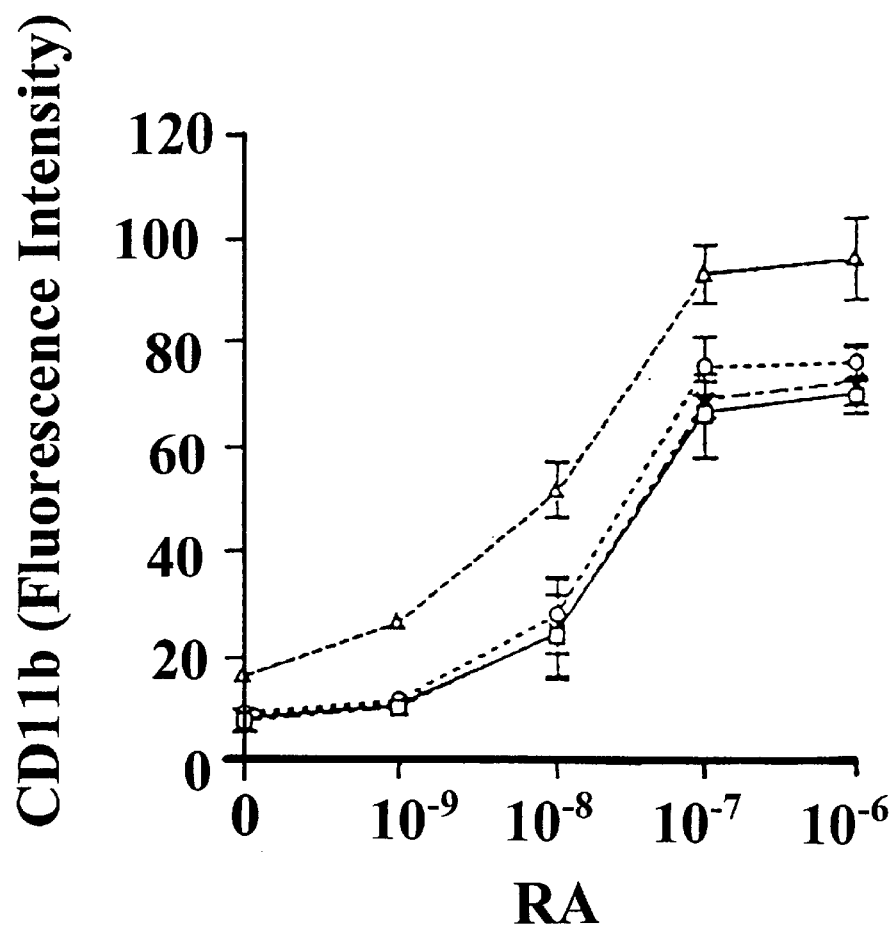
Figure 8D:
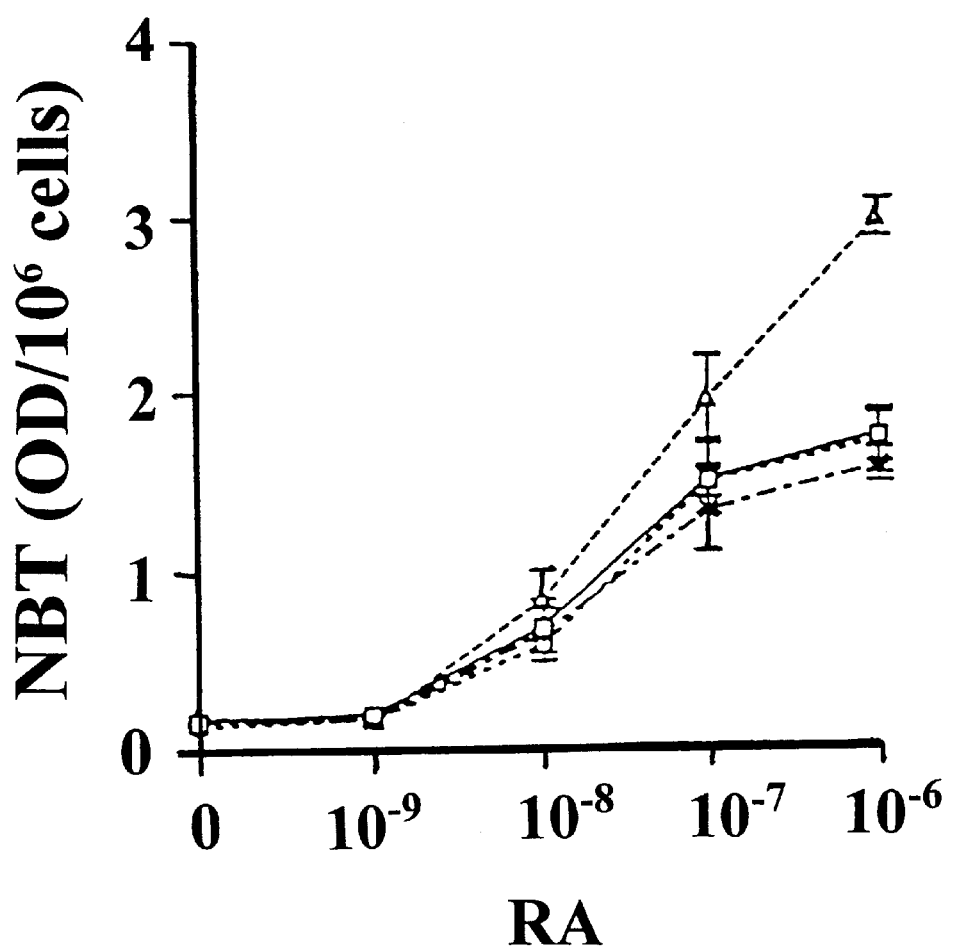

Retinoic acid, both at $10^{-7}$ M and $10^{-6}$ M, had minimal growth inhibitory and differentiating effects on PLZF-retinoic acid receptor-α bone marrow leukaemic cells (FIG. 7E and 7F). Trichostatin A alone showed a marked growth inhibitory effect, but negligible differentiating effect (FIG. 7E and 7F). However, trichostatin A in combination with retinoic acid exerted a striking synergistic growth-inhibitory and differentiating activity (FIG. 7E and 7F). These results demonstrate that combinations of retinoic acid and histone deacetylase inhibitors can revert the X-retinoic acid receptor-α transcriptional repression as well as resistance of PLZF-retinoic acid receptor cells to retinoic acid, and suggest that histone deacetylases activity is required for X-retinoic acid receptor-α leukaemogenic function.

EXAMPLE 25

Cell Culture Studies

NB4 cells incubated with all-trans retinoic acid alone showed dose-dependent induction of differentiation and inhibition of proliferation; however, there was relatively little effect upon induction of apoptosis (FIG. 8). Low concentrations of phenylbutyrate (0.08 mM) had no effect upon proliferation, apoptosis or differentiation of NB4 cells. Relatively high concentrations of phenylbutyrate (2 mM), which were comparable to peak plasma levels transiently attained after completing the drug infusion, induced growth inhibition and mild (15%) induction of apoptosis, but had little effect upon differentiation (FIG. 8). At 10 mM (a concentration that is not clinically achievable), phenylbutyrate completely inhibited proliferation and induced marked apoptosis; no viable cells remained after 4 days of culture. At 0.4 mM, a concentration comparable to that realized during a substantial portion of the treatment period, slight growth inhibition was observed, but there were no effects on other parameters (FIG. 8). Combinations of phenylbutyrate with all-trans retinoic acid produced no significant difference in proliferation or apoptosis compared with phenylbutyrate alone (FIG. 8A and 8B) except at 2 mM phenylbutyrate concentration. However, the combination enhanced cytodifferentiation, as manifested by both an increase in CD11b expression and in NBT reduction (FIG. 8C and 8D).

EXAMPLE 26

Induction of Histone Hyperacetylation

Figure 9:
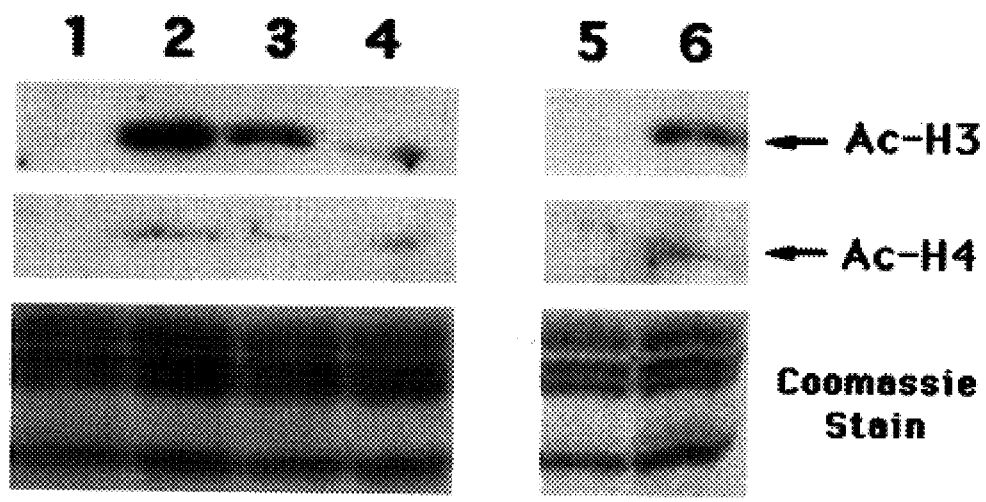
FIG. 9 shows western blot analysis of acetylated histones H3 and H4 in blood and bone marrow mononuclear cells. Hyperacetylation was detected using antiacetylated H3 or H4 antibodies reacting with histones that were acid-extracted from nucleated cells in peripheral blood before (lane 1) and 2, 4 and 6 hours (lanes 2 to 4) after initiation of the phenylbutyrate infusion, and from bone marrow before (lane 5) and after (lane 6) completion of the infusion. The parallel gel stained with Coomassie blue is a loading control.
Figure 10:
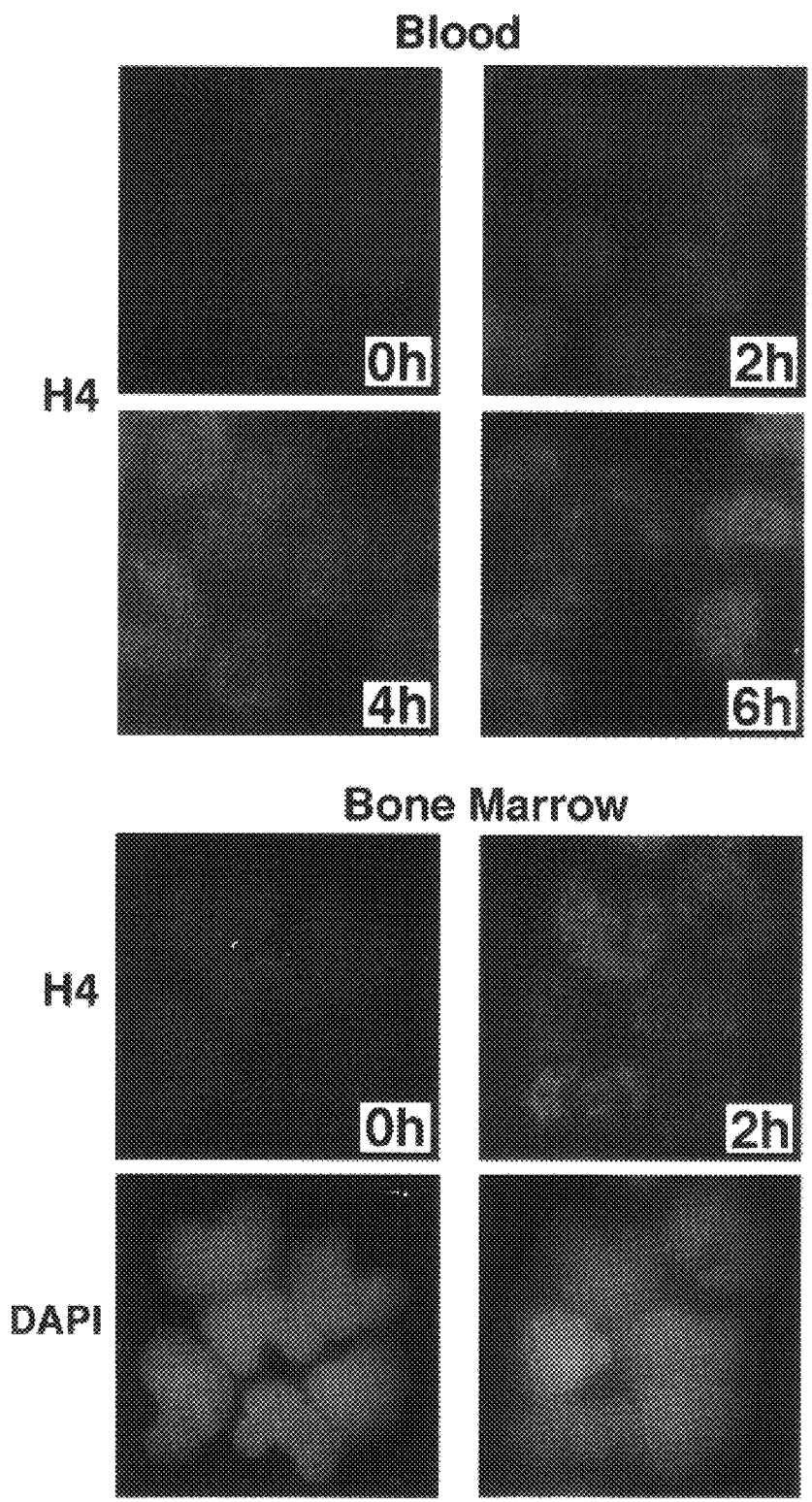
FIG. 10 shows immunofluorescence staining of acetylated histone H4 in peripheral blood mononuclear cells at 0, 2, 4, and 6 hours after a phenylbutyrate infusion (top panels), and bone marrow mononuclear cells before and after infusion (bottom panels). Acetylated histone H4 (red fluorescence) are negative or demonstrate weak positive staining in cells before treatment. The percentage of positive staining cells and the staining intensity progressively increases from baseline up to 6-hours, indicating increasing hyperacetylation of histone H4 after phenylbutyrate treatment. Staining with 4',6-diamidino-2-phenylindole (DAPI) shows the location of cellular nuclei.

Western blot analysis of isolated histones (FIG. 9) showed that the acetylated forms of H3 and H4 were undetectable at baseline in mononuclear cells obtained from the patient's peripheral blood and bone marrow. Two hours after beginning the phenylbutyrate infusion (i.e. coincident with the peak in plasma concentrations), the levels of acetylated H3 and H4 had markedly increased. Immunofluorescence staining of nuclei for acetylated histone H4 showed that hyperacetylation was still visually evident in peripheral blood cells 6 hours after starting the infusion (i.e. approximately 4 hours after discontinuing the drug) (FIG. 10); however, Western analysis showed that the magnitude of this effect had greatly diminished by this time (FIG. 9). Similar effects were observed in bone marrow mononuclear cells. The nuclear location of the immunofluorescence was confirmed by staining with 4',6-diamidino-2-phenylindole (DAPI) (FIG. 10).

EXAMPLE 27

Clinical Effects

Figure 11:
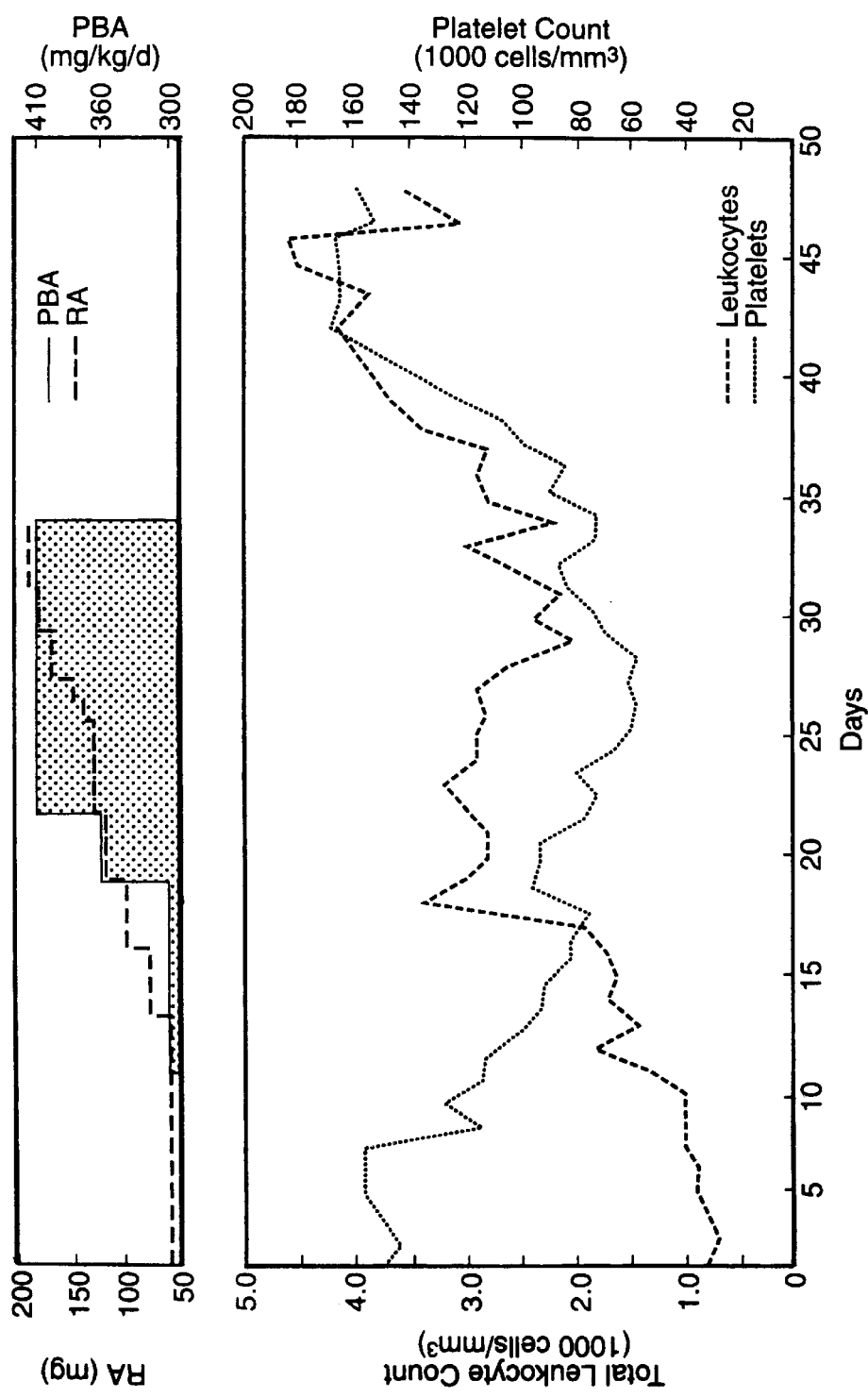
FIG. 11 shows clinical course in a patient with acute promyelocytic leukemia treated with phenylbutyrate and all-trans retinoic acid. The top chart represents days on which various doses of all-trans retinoic acid (RA) (left axis, solid line) and phenylbutyrate (PBA) (right axis, shaded area) were administered. The bottom chart shows the absence of change in the peripheral blood leukocyte count (left axis) and progressive decline in platelet count (right axis) during treatment with all-trans retinoic acid alone, followed by progressive improvement in both parameters after introduction of phenylbutyrate on day 12. The patient attained complete remission by all clinical parameters on day 28.

During the first 11 days of treatment with all-trans retinoic acid alone, the patient's platelet count fell progressively (FIG. 11), a repeat bone marrow showed no improvement, and she was then started on sodium phenylbutyrate. Over the next 23 days, the dose of both all-trans retinoic acid and phenylbutyrate was progressively escalated to maximum doses of 90 mg/m$^2$ and 210 mg/kg BID, respectively. A bone marrow aspirate done 13 days after starting phenylbutyrate (i.e. day 24) showed a reduction in the cumulative percentage of blasts plus promyelocytes from 23% to 9%. A followup bone marrow on day 34 showed complete elimination of leukemic cells, with a residual total of 2% blasts and 2% promyelocytes. Quinacrine-banded cytogenetics revealed a 46 XY karyotype in 20 cells examined, indicating their derivation from the patient's brother. However, an RT-PCR assay for PML/RAR-α was positive, indicating the presence of residual disease. After three weeks off treatment, the patient returned for a second cycle of therapy, using both drugs administered at the highest dose from the initial treatment course. A bone marrow aspirate performed on day 11 of the second treatment course revealed that the RT-PCR test had converted to negative. The patient completed the second 21-day course of treatment and was discharged. As of the last followup date, she remains in complete remission with normal blood counts.

EXAMPLE 28

Summary

In an attempt to understand the role of PML-retinoic acid receptor-α and PLZF-retinoic acid receptor-α fusion proteins in APL pathogenesis and in mediating responses to retinoic acid, the phenotype of PML-retinoic acid receptor-α and PLZF-retinoic acid receptor-α transgenic mice were examined on a comparative basis as to how these phenotypes were influenced by retinoic acid treatment. Concomitantly, the molecular basis of the aberrant response to retinoic acid in APL was investigated. These results indicate that X-retinoic acid receptor-α proteins play a fundamental role either in leukaemogenesis or in modulating retinoic acid responses in APL. These molecules, however, are not sufficient to cause full blown leukaemia. Furthermore, X-retinoic acid receptor-α molecules are not identical to retinoic acid receptor-α mutants, and it is the X portion which confers to the X-retinoic acid receptor-α proteins a different biological role and the ability to cause differential responses to retinoic acid. These findings support a new and unifying model, by which APL pathogenesis is due to the ability of X-retinoic acid receptor-α proteins to repress transcription in a dominant negative manner through aberrant interactions with the transcriptional repression machinery. These data also implicate nuclear receptor co-repressors and histone deacetylases in human cancer and have, in turn, direct implications for the treatment of APL.

EXAMPLE 29
The PML-RAR and PLZF-Retinoic Acid Receptor in Leukaemogenesis

The fact that both PML-retinoic acid receptor-α and PLZF-retinoic acid receptor-α transgenic mice develop leukaemia demonstrate that both X-retinoic acid receptor-α proteins play a crucial role in APL pathogenesis. However, PLZF-retinoic acid receptor-α activity, similar to PML-retinoic acid receptorpα$^{32,38,39}$, seems necessary, but not sufficient, to cause full-blown leukaemia in mice, since in both cases, the leukaemia has a late onset. This observation suggests that X-retinoic acid receptor-α proteins are not sufficient to cause full-blown APL in human patients as well, and that additional mutations are needed, which in humans may consist of the expression of retinoic acid receptor-αX products. The importance of the retinoic acid receptor-αX chimeras in APL leukaemogenesis has been highlighted by the identification of APL cases with non-reciprocal translocations resulting in the expression of the retinoic acid receptor-α-PML fusion gene but lacking the PML-retinoic acid receptor-α fusion gene[40]. Alternatively, in mice, the relative level of expression of the X-retinoic acid receptor-α transgene with respect to the X and retinoic acid receptor-α/retinoid-X-receptor-α genes, and/or other genes, is not sufficient to confer to the X-retinoic acid receptor-α fusion protein the ability to dominantly interfere with their functions. The second interpretation is unlikely because the expression of the X-retinoic acid receptorα transgene is not negligible, as evaluated by Northern blot analysis from mice in the leukaemic phase, and is high enough to dislocate PML and PLZF from the Nbs (FIGS. 1 and 2).

Furthermore, follow up (one year to date) of heterozygous and homozygous PLZF-retinoic acid receptor-α transgenic mice, did not show a difference in onset or incidence of leukaemia between these two groups, once again supporting the first interpretation. On the other hand, both PML-retinoic acid receptor-α and PLZF-retinoic acid receptor-α seem sufficient to cause the MPD that precedes overt leukaemia, since this is observed in 100% of the cases in transgenic mice. The expansion of the promyelocytic cellular compartment would then favor the occurrence of additional transforming events. However, due to the fact that the MPD cannot be detected at birth, it is possible that other molecular events are also needed in order to cause the MPD itself. The interbreeding of X-retinoic acid receptorα and retinoic acid receptor-α-X transgenic mice allow an understanding of whether these molecules are concomitantly necessary to trigger full-blown leukaemia and/or MPD.

EXAMPLE 30
X-Retinoic Acid Receptor-α Proteins Are Not Identical Retinoic Acid Receptor-α Mutants The comparative analysis of the myeloproliferative disorder and leukaemia in X-retinoic acid receptor-α transgenic mice unravels the molecular diversity of X-retinoic acid receptor-α proteins. The most striking evidence of the different biological activity of X-retinoic acid receptor-α proteins is their ability to cause retinoic acid sensitive and retinoic acid resistant leukaemia, which is accruable to their X moiety. Another remarkable difference is the fact that the two molecules can cause similar, but not identical, diseases. The main feature which distinguishes the biological role of X-retinoic acid receptor-α proteins in vivo is the absence of a block at the promyelocytic stage of myeloid differentiation in the MPD and leukaemia from hCG-PLZF-retinoic acid receptor-α transgenic mice, and the presence of this differentiation block, even if not absolute, in the MPD and leukaemia from hCG-PML-retinoic acid receptor-α transgenic mice (FIGS. 3A and 3B and reference 32). Since the presence of PLZF-retinoic acid receptor-α does not cause promyelocytic-like leukaemia in transgenic mice, this data may suggest that human t(11;17) APL could result from the concomitant activity of PLZF-retinoic acid receptor-α and retinoic acid receptor-α-PLZF fusion proteins. The interbreeding of PLZF-retinoic acid receptor-α and retinoic acid receptor-α-PLZF transgenic mice can facilitate this understanding.

EXAMPLE 31
Transcriptional Silencing in APL Pathogenesis

In the absence of the ligand, nuclear receptors, such as thyroid receptors and retinoic acid receptors, form multiprotein complexes with co-repressors SMRT and N-CoR, mammalian homologues of the yeast transcriptional repressor Sin3 (mSin3A or mSin3B) and histone deacetylase (histone deacetylases 1 or 2)[15]. As shown herein, the X-retinoic acid receptor-α proteins can also interact with the nuclear receptor co-repressors, SMRT and N-CoR, and histone deacetylase inhibitors, and in combination with retinoic acid, can overcome their transcriptional repressive activity as well as the retinoic acid unresponsiveness of PLZF-retinoic acid receptor-α leukaemic cells. This suggests that the transcriptional repression ability of X-retinoic acid receptor-α proteins is, at least in part, linked to histone deacetylase activity. Recently, using in vitro GST-pull down experiments, Hong et al. have shown that even in the presence of micromolar concentrations of retinoic acid, there was a small degree of association between SMRT and PML-retinoic acid receptor-α or PLZF-retinoic acid receptor-α, with the latter chimeric protein forming a somewhat more stable complex[41]. The complex of SMRT with the PLZF-retinoic acid receptor-α fusion protein is considerably more stable (or insensitive to retinoic acid) than with PML-retinoic acid receptor-α. Taken together, these results suggest that the lack of responsiveness of t(11;17) APL to retinoic acid results from the ligand insensitive interaction of co-repressors with the N-terminal PLZF moiety of the fusion protein. It is also possible that retinoic acid receptor-α-PLZF, which can act as an aberrant version of PLZF[12], contributes to retinoic acid unresponsiveness in t(11;17) APL through a retinoic acid receptor-α/retinoid-X-receptor-α independent pathway. Although not as striking as that of PLZF-retinoic acid receptor-α, PML-retinoic acid receptor-α also displays a co-repressor association less sensitive to retinoic acid[41]. However, no association between the co-repressors and the wild type PML protein was detected in these experiments suggesting that another factor(s) which is capable of simultaneously contacting both the PML moiety of the PML-retinoic acid receptor-α fusion protein and the co-repressors, may be required to stabilize this interaction. In this respect, it is worth noting that the PML-retinoic acid receptor-α, through its PML moiety, physically interacts and co-localizes with the wild type PLZF (FIG. 2 and reference 13), thus implying that the PLZF repressor plays a central role in the transcriptional repression mechanisms underlying APL pathogenesis. However, pharmacological doses of retinoic acid can overcome PML-retinoic acid receptor-α transcriptional repressive activity as demonstrated by the fact that on certain promoters, PML-retinoic acid receptor-α can act as a dominant negative repressors at physiological doses of retinoic acid, and as a potent transcriptional activator in the presence of $10^{-6}$ M retinoic acid[5]. This notion is further supported by the fact that the de novo resistance to retinoic acid can be due to mutations in the ligand binding domain of the PML-retinoic acid receptor-α fusion protein. In addition, since Sin3/N-CoR/histone deacetylases are also required for transcriptional repression by the mad/max complex, which is linked with cellular differentiation, both X-retinoic acid receptor-α proteins may also contribute to leukaemogenesis by sequestration of these factors and the inhibition of mad/max function in favor of the growth promoting myc/max function[42-45].

EXAMPLE 32
Acquired Resistance to Retinoic Acid in APL

Although de novo, in vitro acquired retinoic acid resistance in APL-derived cell lines such as NB4 has been attributed to several factors including the loss of an intact PML-retinoic acid receptor-α fusion proteins[46] or mutations in the retinoic acid binding domain of the PML-retinoic acid receptor-α chimeras[47], in vivo, the mechanisms underlying acquired retinoic acid resistance in APL patients have remained elusive. About 25% of the APL patients showing an acquired resistance to retinoic acid also harbor mutations in the retinoic acid ligand binding domain of the PML-retinoic acid receptor fusion protein[48]. However, in the remaining 75% of patients, no mutations have been found in the PML-retinoic acid receptor-α, PML, or retinoic acid receptor-α genes[48]. Thus, in the remaining APL cases, retinoic acid resistance may be conferred by somatic mutation occurring in the APL blasts that would further stabilize the interaction between X-retinoic acid receptor-α proteins and nuclear receptor co-repressors, or that would enhance the activity of histone deacetylasess in these complexes.

The present findings demonstrate that a high dose retinoic acid therapy is effective in inducing complete clinical remission in leukaemia from hCG-PLZF-retinoic acid receptor-α transgenic mice. This supports the concept that higher retinoic acid concentrations might be required to release the PLZF-retinoic acid receptor-α/nuclear co-repressor complex and overcome its dominant negative action on the transcriptional activity of the normal retinoic acid receptor-α/retinoid-X-receptor-α complexes. An attractive implication of these findings for APL treatment would be to use a combination therapy of low doses of specific inhibitors of histone deacetylases such as trichostatin A[31], trapoxin[31], or butyrates[49] in combination with retinoic acid This approach would antagonize X-retinoic acid receptor-α transcriptional repression and concomitantly induce the retinoic acid dependent transactivation of retinoic acid target genes by retinoic acid receptor-α/retinoid-X-receptor-α and/or by X-retinoic acid receptor-α proteins themselves. Specific inhibitors of histone deacetylases have already been used in the treatment of malaria, toxoplasmosis and β-thalassemia[50,51]. In APL, this treatment would represent the first example of "transcription therapy" for cancer.

Discussion

This study strongly suggests a clinical link between histone deacetylase and oncogenic targeting of transcriptional repression, both as a critical mechanism of carcinogenesis and as a molecular target for anticancer therapy. In acute promyelocytic leukemia, a chromosomal translocation fuses genes that encode a nuclear retinoic acid receptor (RAR-α) with a transcription factor, known as PML[76]. All-trans retinoic acid can relieve the maturational block caused by this molecular defect and will induce differentiation of the malignant cell[34,35,77]. Used alone, however, this drug is not curative, and patients treated solely with this agent eventually relapse and become resistant to further retinoid treatment[2].

Histone acetylation appears critically involved in the activation of an increasingly recognized number of genes[15,61-64,78,79]. Conversely, histone deacetylation has been linked to gene repression, but the molecular mechanisms have been unclear, particularly as they relate to sequence-specific transcriptional repression by oncogenes. Recently, however, the mammalian homologue of a yeast protein known as Sin-3 was shown to bind a protein known as N-CoR (for Nuclear Co-Repressor)[53,80,81]. This complex then recruits a factor with histone deacetylase (HDAC) activity[42,47] and suppresses gene activation.

The PML/RAR-α fusion protein of acute promyelocytic leukemia was shown to recruit the mSin-3/N-CoR/HDAC complex and to suppress the normal pathway of retinoic acid signaling[65,67]. All-trans retinoic acid displaced the repressor complex in retinoid-sensitive but not retinoid-resistant NB4 cells in vitro. However, co-treatment with all-trans retinoic acid plus trichostatin A (the prototypic inhibitor of histone deacetylase) displaced the repressor complex and restored the differentiating effect, even in variants of leukemic cells that were inherently retinoid resistant[65-67]. More generally, similar mechanisms have recently been discovered in other cancer cell types, including myeloid leukemias[82,83] and malignant lymphomas[84], and also in the myc/mad/max signaling pathway[45,47,85-87]. Furthermore, a link between gene methylation, a recognized mechanism of transcriptional repression, and histone deacetylation has now been established via a protein known as MeCP2, which binds the mSin-3/HDAC complex to methylated cytosines[87]. Thus, the targeting of this enzymatic process has potential therapeutic implications beyond acute promyelocytic leukemia.

A second important finding is the observation that histone deacetylase can be safely inhibited in vivo. A major clinical constraint in the field of "differentiation therapy" has been a perception (inferred from cell culture studies) that high plasma drug concentrations must be sustained in order to induce the differentiating effect. In the past, such levels have proved difficult to sustain or were excessively toxic in human subjects[88,89]. By using the twice-per-day bolus dosing schedule with an intravenously administered drug, one can maximize peak concentrations of phenylbutyrate, coincident with the peak plasma level of all-trans retinoic acid. This dosing schedule clearly induced hyperacetylation of histones in the target tissues (i.e. blood and bone marrow). Moreover, the time-dependence and reversibility of this activity (FIGS. 9 and 10) showed that high concentrations need not be sustained in order to transiently achieve both the desired biological effect and a major clinical response, in this case, elimination of molecular evidence of disease.

Alternative explanations were considered for this clinical observation, including whether the response could have been due to the increased dose of all-trans retinoic acid, to phenylbutyrate alone, or to some mechanism other than inhibition of histone deacetylase. In similar highly resistant patients, increasing the dose of all-trans retinoic acid neither increases the plasma concentration nor recaptures the clinical response[2]. The magnitude of this response is also unusual, since less than 15% of newly diagnosed retinoid-naive patients convert their RT-PCR assay to negative with retinoid therapy alone[90]. The present in vitro studies showed that the single-agent activity of phenylbutyrate was limited (FIG. 8), and no major differentiating effects were observed absent the addition of all-trans retinoic acid. Other agents that are chemically quite distinct from phenylbutyrate also inhibit this enzyme and act synergistically with all-trans retinoic acid[74]. Since these drugs have little single-agent activity, some alternative but complementary mechanism must be invoked to account for this activity. Phenylbutyrate has not been clinically useful in patients with myelodysplasia, myeloid leukemia and solid tumors[91,92], but the drug has not been tested in patients with acute promyelocytic leukemia.

"Differentiation therapy" has been proposed as a method of cancer treatment[89,93]. Spontaneous regression and differentiation occurs occasionally in several types of cancer (e.g. teratocarcinomia, neuroblastoma, renal cancer, etc.), and a number of agents induce maturation in tumor cell lines in vitro[92]. Clinically, however, this effect has been reproducibly demonstrated only in acute promyelocytic leukemia with the use of all-trans retinoic acid[2,34,35,77], and earlier expectations that this concept might prove generalizable to other cancers have not yet been realized. However, a number of studies have reported synergistic interactions between retinoids or other agents[65-67,93-95] when combined with compounds that are now known to be inhibitors of histone deacetylase. The present invention suggests a unifying explanation for these observations, and they indicate that "targeted transcription therapy" might be successfully tested in other neoplastic diseases.

The following references were cited herein:
1. Grignani, F. et al. *Blood* 83, 10–25 (1994).
2. Warrell, R. P. et al. *N. Engl. J. Med.* 329, 177–189 (1993).
3. Pandolfi, P. P. *Haematol.* 81, 472–482 (1996).
4. Kalantry, S. et al. *J. Cell. Phys.* 173, 288–296 (1997).
5. Pandolfi, P. P. et al. *Oncogene* 6, 1285–1292 (1991).
6. Kakizuka, A. et al. *Cell* 66, 663–674 (1991).
7. de The, H. et al. *Cell* 66, 675–684 (1991).
8. Goddard et al. *Science* 254, 1371–1374 (1991).
9. Chen, Z. et al. *EMBO J.* 12, 1161–1167 (1993).
10. Pandolfi, P. P. et al. *EMBO J.* 11, 1397–1407 (1992).
11. Reddy, et al. *Trends Biochem. Sci.* 17, 344–345 (1992).
12. Li, J. Y. et al. *J. Biol. Chem.* 272, 22447–22455 (1997).
13. Koken, et al. *Proc. Natl. Acad. Sci. USA* 94, 10255–10260 (1997).
14. Chambon, P. *Faseb J.* 10, 940–954 (1996).
15. Grunstein, M. *Nature* 389, 349–352 (1997).
16. Smith, M. A. et al. *J. Clin. Oncol.* 10, 839–864 (1992).
17. Gudas, L., Sporn, M. & Roberts, A. in *The Retinoids: Cellular biology and biochemistry of the retinoids.* 443–520 (Raven Press, New York, 1994).
18. Fenaux, P. et al. *Sem. Onc.* 24, 92–102 (1997).
19. Licht, J. D. et al. *Blood* 85, 1083–1094 (1995).
20. Perez, A. et al. *EMBO J.* 12, 3171–3182 (1993).
21. Jansen, J. H. et al. *Proc. Natl. Acad. Sci. USA* 92, 7401–7405 (1995).
22. Licht, J. D. et al. *Oncogene* 12, 323–336 (1996).
23. Dong, S. et al. *Proc. Natl. Acad. Sci. USA* 93, 3624–3629 (1996).
24. Kastner, P. et al. *EMBO J.* 11, 629–642 (1992).
25. Chen, Z. et al. *Proc. Natl. Acad. Sci. USA* 91, 1178–1182 (1994).
26. Dyck, J. et al. *Cell* 76, 333–343 (1994).
27. Koken, M. H. M. et al. *EMBO J.* 13, 1073–1083 (1994).
28. Weis, K. et al. *Cell* 76, 345–356 (1994).
29. Nervi, C. et al. *Cancer Res.* 52, 3687–3692 (1992).
30. Ruthardt, M. et al. *Mol. Cell. Biol.* 17, 4859–4869 (1997).
31. Yoshida, et al. *Bioessays* 17, 423–430 (1995).
32. He, L.-Z. et al. *Proc. Natl. Acad. Sci. USA* 94, 5302–5307 (1997).
33. Goldman, J. M. *Curr. Opin. Hematol.* 4, 277–285 (1997).
34. Warrell, R. P., Jr. et al. *N. Engl. J. Med* 324, 1385–1393 (1991).
35. Castaigne, S. et al. *Blood* 76, 1704–1709 (1990).
36. Chen, S.-J. et al. *J. Clin. Invest.* 91, 2260–2267 (1993).
37. Jansen, J. H. et al. *Blood* 88, #3421, 3173b (1996).
38. Grisolano, J. L. et al. *Blood* 89, 376–387 (1997).
39. Brown, D. et al. *Proc. Natl. Acad. Sci. USA* 94, 2551–2556 (1997).
40. Lafage-Pochitaloff, M. et al. *Blood* 85, 1169–1174 (1995).
41. Hong et al. *Proc. Natl. Acad. Sci. USA* 94, 9028–9033 (1997).
42. Heinzel, T. et al. *Nature* 387, 43–48 (1997).
43. Alland, L. et al. *Nature* 387, 49–55 (1997).
44. Hassig, C. A. et al. *Cell* 89, 341–347 (1997).
45. Laherty, C. D. et al. *Cell* 89, 349–356 (1997).
46. Dermime, S. et al. *Blood* 82, 1573–1577 (1993).
47. Shao, W. et al. *Blood* 89, 4282–4289 (1997).
48. Ding, W. et al. *Blood* 90, 415a (1997).
49. Lea, M. A. & Tulsyan, N. *Anticancer. Res.* 15, 879–883 (1995).
50. Darkin-Rattray, S. J. et al. *Proc. Natl. Acad. Sci. USA* 93, 13143–13147 (1996).
51. Collins, A. F. et al. *Blood* 85, 43–49 (1995).
52. Rousselot, P. et al. *Oncogene* 9, 545–551 (1994).
53. Horlein, A. J. et al. *Nature* 377, 397–404 (1995).
54. Gaub, M. P. et al. *Exp. Cell Res.* 201, 335–346 (1992).
55. Borden, K. L. B. et al. *EMBO J.* 14, 1532–1541 (1995).
56. Chomczynski, P. & Sacchi, N. *Anal. Biochem.* 162, 156–159 (1987).
57. Longo, L. et al. *J. Exp. Med.* 172, 1571–1575 (1990).
58. Sambrook, et al. *Molecular cloning: a laboratory manual.*, (Cold Spring Harbor Laboratory Press, Plainview, N.Y., 1989).
59. Dignam, et al., *Nucl. Acids. Res.* 11, 1475–1489 (1983).
60. Ye et al. *Nature Genetics,* 16:161–170 (1997).
61. Lee D Y et al. *Cell* 1993; 72:73–84.
62. Yang X et al. *Nature* 1996; 382:319–24.
63. Ogryzko V V et al. *Cell* 1996; 87:953–9.
64. Bannister A J, Kouzarides T. *Nature* 1996; 384:641–3.
65. Lin R J et al. *Nature* 1998; 391:811–4.
66. Grignani F et al. *Nature* 1998; 391:815–8.
67. He L-Z et al. *Nature Genetics* 1998; 18:126–35.
68. Candido E P M et al. *Cell* 1978; 14:105–13.
69. Dover G J et al. *N Engl J Med.* 1992; 327:569–70.
70. Maestri N E et al. *N Engl J Med.* 1996; 335; 855–9.
71. Lanotte M et al. *Blood* 1991; 77:1080–5.
72. Vermes I et al. *J Immunol Meth.* 1995; 184:39–51.
73. Zhu J et al. *Leukemia* 1995; 9:302–9.
74. Richon V M et al. *Proc Natl Acad Sci (USA)* 1998; 95:3003–7.
75. Miller W H Jr. et al. *Blood* 1993; 82:1689–94.
76. de Thé H et al. *Nature* 1990; 347:558–61

77. Huang M E et al. *Blood* 1988; 72:567–2.
78. Wolffe A P, Pruss D. *Cell* 1996; 84:817–9.
79. Ptashne M, Gann A. *Nature* 1997; 386:569–76.
80. Kurokawa R et al. *Nature* 1995; 377:451–4.
81. Chen J D, Evans R. M. *Nature* 1995; 377:454–7.
82. Borrow J et al. *Nature Genetics* 1996; 14:33–41.
83. Sobulo O M et al. *Proc Natl Acad Sci (USA)* 1997; 94:8732–7.
84. Dhordain P et al. *Proc Natl Acad Sci (USA)* 1997; 94:10762–7.
85. Ayer D E et al. *Cell* 1995; 80:767–76.
86. Schreiber-Agus, N et al. *Cell* 1995;80:777–86.
87. Nan X et al. *Nature* 1998; 393:386–9.
88. Thibault A et al. *Cancer Res* 54:1690–1694, 1994.
89. Andreeff M et al. *Blood* 1992; 80:2604–9.
90. Jurcic J G et al. *Blood (Suppl.)* 1996; 88:635a.
91. Gore S D et al. *Blood (Suppl.)* 1996; 88:582a.
92. Carducci M et al. *Proc. Am. Soc. Clin. Oncol.* 1998; 17:215a.
93. Ferrari A C, Waxman S: Differentiation agents in cancer therapy, in *Cancer Chemotherapy and Biological Response Modifiers Annual*, eds. Pinedo H M, Longo D L, Chabner B A, Elsevier Science, New York, pp. 337–366, 1994.
94. Weng L J et al. *Blood (Suppl.)* 1996; 90:329a.
95. Sidell N et al. *Exp Cell Res* 1998; 239:169–74.
96. Pineau T et al. *Biochem Pharmacol* 1996; 52:659–67.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating acute promyelocytic leukemia ("APL") in an individual, comprising the step of administering to said individual a pharmacologically effective dose of retinoic acid and sodium phenylbutyrate, so as to thereby treat APL.

2. The method of claim 1, wherein said sodium phenylbutyrate is administered in a dose of from about 5 mg/kg body weight to about 1,000 mg/kg body weight.

3. The method of claim 1, wherein said retonic acid is administered in a dose of from about 0.05 mg/kg to about 7.5 mg/kg.

* * * * *